(12) United States Patent
Black et al.

(10) Patent No.: US 7,778,695 B2
(45) Date of Patent: Aug. 17, 2010

(54) IN VIVO FLUORESCENCE SENSORS, SYSTEMS, AND RELATED METHODS OPERATING IN CONJUNCTION WITH FLUORESCENT ANALYTES

(75) Inventors: Robert D. Black, Chapel Hill, NC (US); Natasha Bolick, Creedmoor, NC (US)

(73) Assignee: Sicel Technologies, Inc., Morrisville, NC (US)

( * ) Notice: Subject to any disclaimer, the term of this patent is extended or adjusted under 35 U.S.C. 154(b) by 0 days.

(21) Appl. No.: 12/389,012

(22) Filed: Feb. 19, 2009

(65) Prior Publication Data

US 2009/0180962 A1    Jul. 16, 2009

Related U.S. Application Data

(62) Division of application No. 10/779,907, filed on Feb. 17, 2004, now Pat. No. 7,510,699.

(60) Provisional application No. 60/448,349, filed on Feb. 19, 2003, provisional application No. 60/471,706, filed on May 19, 2003.

(51) Int. Cl.
  *A61B 6/00*    (2006.01)
(52) U.S. Cl. .................. 600/476; 424/9.1; 424/9.6; 424/426
(58) Field of Classification Search ............... 424/9.1, 424/9.6, 426; 600/476
See application file for complete search history.

(56) References Cited

U.S. PATENT DOCUMENTS 4,976,266 A    12/1990 Huffman et al.

(Continued)

FOREIGN PATENT DOCUMENTS

DE    332075    1/1984

(Continued)

OTHER PUBLICATIONS

Barthe, Jean, *Electronic dosimeters based on solid state detectors*, Nuclear. Instruments. and Methods in Physics Research Sec. B vol. 184, pp. 158-189 (2001).

(Continued)

*Primary Examiner*—Brian Casler
*Assistant Examiner*—John F Ramirez
(74) *Attorney, Agent, or Firm*—Myers Bigel Sibley & Sajovec, P.A.

(57) ABSTRACT

Methods, systems, devices and computer program product include: (i) administering a fluorescent analyte to a subject; (ii) repetitively emitting excitation light from an implanted sensor over a desired monitoring period; (iii) detecting fluorescence intensity in response to the excitation light using the implanted sensor that outputs the excitation light; and (iv) using data associated with the detected fluorescence intensity to perform at least one of: (a) calculate the concentration or dose of the analyte received proximate to the implanted sensor site; (b) evaluate the pharmacodynamic or pharmacokinetic activity of the fluorescent analyte; (c) confirm Ab attachment to a tumor site; (d) monitor a non-target site to confirm it is not unduly affected by a therapy; (e) monitor for changes in cellular properties; (f) use the calculated dose or concentration data to adjust or customize a therapeutic amount of the analyte administered to the subject; (g) confirm micelle concentration at a target site and then stimulate toxin release based on the confirmation; and (h) monitor for the expression of a protein produced from a gene therapy modification.

In particular embodiments, the intensity of the excitation signals emitted to the localized tissue can be varied in a predetermined manner to generate optical profiling data of the response of the tissue proximate the sensor.

29 Claims, 14 Drawing Sheets

U.S. PATENT DOCUMENTS

| | | | |
|---|---|---|---|
| 5,159,262 | A | 10/1992 | Rumbaugh et al. |
| 5,166,073 | A | 11/1992 | Lefkowitz et al. |
| 5,341,805 | A | 8/1994 | Stavridi et al. |
| 5,596,199 | A | 1/1997 | McNulty et al. |
| 5,833,603 | A | 11/1998 | Kovacs et al. |
| 6,070,096 | A | 5/2000 | Hayashi |
| 6,330,464 | B1 | 12/2001 | Colvin et al. |
| 7,096,053 | B2 | 8/2006 | Loeb et al. |
| 2002/0102212 | A1 | 8/2002 | Black |
| 2004/0011671 | A1 | 1/2004 | Shults et al. |
| 2004/0054385 | A1 | 3/2004 | Lesho |

FOREIGN PATENT DOCUMENTS

| | | |
|---|---|---|
| EP | 0471957 A2 | 2/1992 |
| GB | 2263196 A | 7/1993 |
| WO | WO00/18294 | 6/2000 |
| WO | WO00/33065 | 6/2000 |
| WO | WO00/40299 | 7/2000 |
| WO | WO02/09775 | 2/2002 |

OTHER PUBLICATIONS

Butson, Martin J. et al, *A new radiotherapy surface dose detector: The MOSFET*, Medical Physics, American Institute of Physics, vol. 23 (5) pp. 655-658 (May 1996).

Mathur, V.K, *Ion storage dosimetry*, Nuclear Instruments and Methods in Physics Research B, vol. 184 pp. 190-206 (2001).

Mayinger et al., *Endoscopic Fluorescence Spectroscopy in the Upper GI Tract for the Detection of GI Cancer: Initial Experience*, The American Journal of Gastroenterology, vol. 96, No. 9, Sep. 2001, pp. 2616-2621.

Moreno, D.J. et al, *A Simple Ionizing Radiation Spectrometer/Dosimeter based on Radiation Sensing Field Effect Transistors (RadFETs)* TRANSDUCERS '97 International Conference on Solid-State Sensors and Actuators Chicago, pp. 1283-1286 (Jun. 16-19, 1997).

International Search Report corresponding to PCT/US2004/005785, dated Feb. 22, 2005.

Soubra, M. et al., *Evaluation of a dual bias dual metal oxide-silicon semiconductor field effect transistor detector as radiation dosimeter*, American Assoc. Phys. Med., vol. 21, No. 4, pp. 567-572, Apr. 1994.

Tarr, N.G. et al., *A Floating Gate MOSFET Dosimeter Requiring No External Bias Supply* Redecs 97. Fourth European Conference on Radiation and Its Effects on Components and Systems (Cat. No. $97^{TH}8294$), pp. 277-281 (1998).

Transmittance of light vs. wavelength through dog blood and serum. The times noted are the integration time of the multichannel analyzer.

Components of the current fiber optic probe: laptop, multichannel analyzer, and fiber optic probe.

Microscope view of Raji human lymphoma cells (in pellet form) labeled with Alexa Fluor 647 conjugated to anti-CD20.

Figure 5A was taken with 647 nm, thus showing the primary antibody labeling. Figure 5B image was taken at 568nm, thus showing the secondary antibody labeling.

Clearance curve after fluor administered in rat tail vein at time 0. Plots of signal (320 ms integration time) at three different time points: 30 seconds (highest intensity), 11 min., 45 min.

Alexa 647 labeled Herceptin uptake in nude mouse with human BT474 scapular and flank tumors. Time of injection is 0:00.

Figures 9A and 9B: Side and end view schematics of the diode-based sensor in glass capsule (dimensions in mm)

IN VIVO FLUORESCENCE SENSORS, SYSTEMS, AND RELATED METHODS OPERATING IN CONJUNCTION WITH FLUORESCENT ANALYTES

RELATED APPLICATIONS

The present application is a divisional of application Ser. No. 10/779,907, filed Feb. 17, 2004, now U.S. Pat. No. 7,510,699 which claims priority to U.S. Provisional Application Ser. No. 60/448,349, filed Feb. 19, 2003 and U.S. Provisional Application Ser. No. 60/471,706, filed May 19, 2003, the entire contents of the above-referenced documents are hereby incorporated herein by reference.

BACKGROUND

The use of fluorescent reporters to study cells and tissue is known and a body of work has grown up around this technique. Most of this work, however, deals with ex vivo samples and application to living tissue in vivo is difficult given the fluorescence microscopy tools presently available.

The use of therapeutic antibodies ("Ab") in cancer treatment is a relatively new endeavor. Several compounds are now approved for use in the United States (e.g., HERCEPTIN, RITUXAN, ZEVALIN) and more are in development. These compounds are restricted to treating refractory diseases and are not presently used as a first-line treatment. A factor in this disposition of Ab therapies is the lack of clear knowledge of effect. To be effective, the Ab therapy should be selective in attaching to the target and stay attached to the target sufficiently long to exert or induce a clinical effect. There is no currently viable or acceptable method by which such measurements of clinical effect can be made in vivo in target tissue.

The phenomenon of fluorescence is well studied and understood. As applied in biology, the focus is generally on choosing compounds that fluoresce at convenient wavelengths, have certain molecular weights, bind to a substrate in a certain way, resist photobleaching and the like For example, many commercial fluors (e.g., the ALEXA series from Molecular Probes, Eugene, Oreg.) are in the 500-900 Dalton range, whereas green fluorescent protein is nearly 30,000 Daltons. The fluorophores can either be conjugated with a substrate molecule, or activated or bound indirectly. Some compounds of interest, e.g., DOXORUBICIN, are naturally fluorescent, though the strength of the fluorescence may not be optimal for monitoring purposes. The ability to probe different fluors at different wavelengths is desired in that it may allow for intricate, multi-faceted labeling studies.

A significant volume of work has been done to map optical properties of tissues in the body with endoscopic techniques as discussed in, for example, *Potential New Endoscopic Techniques for the Earlier Diagnosis of Pre-Malignancy* by Rollins et al., Best Pract Res Clin Gastroenterol, 15(2):227-47 (2001). In general, researchers have assessed tissue absorption and endogenous fluorescence spectra in an attempt to create characteristic signatures of, say, benign or malignant tissue. For example, adenomatous colon polyps were examined by diffuse reflectance spectroscopy as discussed in *Diffuse Reflectance Spectroscopy of Human Adenomatous Colon Polyps in Vivo* by G. Zonios et al., Applied Optics 38(31): 6628-37 (1999). Autofluorescence spectroscopy has been used for the characterization of esophageal cancer (*Light-Induced Autofluorescence Spectroscopy for the Endoscopic Detection of Esophageal Cancer*, B. Mayinger, Gastrointest Endosc 54(2):195-201 (2001)), colonic polyps (Colonic Polyp Differentiation Using Time-Resolved Autofluorescence Spectroscopy, M. Mycek, Gastrointest Endosc 48(4): 390-4 (1998)), and head and neck cancer (*In Vivo Native Cellular Fluorescence and Histological Characteristics of Head and Neck Cancer*, S. Schantz, Clin Can Res 4(5):1177-82 (1998)). The introduction of exogenous fluors has also been tried (e.g., *Fluorescence Endoscopy of Gastrointestinal Disease Basic Principles, Techniques, and Clinical Experience*, H. Stepp, Endoscopy 30(4):379-86 (1998)), especially as related to photodynamic therapy (e.g., Mayinger, 2001). Unfortunately, following detailed kinetics with endoscopic techniques of this sort would likely be commercially undesirable.

Several approaches have been proposed for in vivo optical imaging in small animals. Anti Cancer, Inc. (San Diego, Calif.) has developed an extensive catalog of probes conjugated to green fluorescent protein (GFP) and has produced images of tumors in vivo in nude mice as discussed in, for example, *Visualizing Gene Expression by Whole-Body Fluorescence Imaging*, M. Yang, Proc Natl Acad Sci 97(22): 12278-12282 (2001). However, due to the strong attenuation and scattering of visible light by tissue, this technique is limited to tumors within a few millimeters of the skin surface. Xenogen Inc. (Alameda, Calif.) proposes the use of a bioluminescent reporter (LUCIFERAN) and a sensitive external camera to image subsurface events, such as the effects of antineoplastic drugs on tumor cells as discussed in *Visualizing the Kinetics of Tumor-Call Clearance in Living Animals* by T. Sweeney, Proc Natl Acad Sci 96(21):12044-9 (1999). Again, this technique is hampered by the attenuation of the light signal by tissue and is thus limited to mice with tumors near the surface. The long integration times required compromise following detailed kinetics. Neither one of these techniques is thought to be transferable to human clinical applications.

Despite the above, there remains a need for systems that can monitor the fluorescence of analytes at clinically useful depths in humans over time.

SUMMARY

The present invention provides methods, systems, devices and computer program products that monitor fluorescent analytes, for example, fluorescently labeled analytes, naturally fluorescent analytes and/or analytes that exhibit fluorescence when introduced to a subject, in vivo to provide a clinically suitable tool for evaluating the fluorescence of the fluorescent analytes at clinically useful depths in subjects, particularly human subjects. In certain embodiments, these depths can be from about 1 cm to about 25 cm or greater, typically between about 5-25 cm, and, in certain embodiments, between about 10-20 cm from the surface.

Embodiments of the present invention can provide probes and systems (such as catheter-based, fiber optic, and/or fully implantable devices) that provide pharmacokinetic and/or dynamic measurements of in vivo fluorescence in target (localized) internal regions.

Embodiments of the present invention can provide cost-effective methods, systems, devices and computer program products that can individualize and customize therapy to improve response and outcome, assess an internal dose received at a target site, and/or otherwise monitor therapeutic response or delivery of fluorescent analytes or compounds in the body. In certain embodiments, the methods, systems, devices and computer program products can provide data regarding the impact of therapies on tumors or normal (non-targeted) tissue.

The present invention provides methods, systems, devices and computer program products for in vivo dynamic monitoring of detected fluorescence, which is emitted from localized tissue in a target region of the body over a selected response or watch period. Generally described, the monitoring can be carried out as a general metabolic assessment, to evaluate or monitor therapy types (including antibody and pharmaceutical therapies)- and/or to obtain data and evaluate metabolic, biokinetic parameters, or predictor variables associated with the in vivo detected fluorescence. The data can be used, inter alia, to: (a) predict or assess the likelihood that a planned treatment will be effective (before and/or after a first or subsequent therapeutic dose is actually administered to the subject); (b) identify which drug or drugs will be likely to provide a suitable clinical response for that subject; (c) monitor intratumoral kinetics; (d) study pharmacokinetics and/or pharmacodynamics; (e) study the impact of modifying agents, treatments, or procedures on drug or antibody uptake and/or retention or tumor kill or morbidity; (f) measure uptake, trapping, or retention of fluor-labeled analytes (for any desired treatment, whether drug or antibody); (g) study an individual's bio-response to a therapy; (h) exclude certain therapy choices; (i) evaluate metabolic activity or behavior; and (j) test for site specific or level of gene or protein expression.

Alternatively, the monitoring may be carried out to quantitatively measure the dose received at localized tissue in the target region. In other embodiments, the present invention can use the detected fluorescence to analyze the pharmacokinetics/pharmacodynamics or in vivo performance of certain pharmaceutical drugs, drug products an/or derivatives thereof, including analytes, antibodies, metabolites or other therapeutic agents in the body.

Advantageously, in certain embodiments, the present invention can provide cost-effective minimally invasive methods, systems, devices and computer program products that can evaluate, in substantially real-time, one or more selected biokinetic parameters or predictor variables of a subject using fluor-data obtained in vivo. Certain embodiments of the devices and systems can be configured to identify the differences in response between normal and malignant tissue and/or the differences in the physiology and biology of individual tumors or tumor sites (or the same tumor site at different times) and to utilize the identified information regarding same to develop individualized treatment decisions, and/or to predict therapeutic outcome and/or alter a therapy to improve tumor response.

In certain embodiments, two different fluor-response profiles of a subject can be generated. The two different profiles can be obtained before and/or after certain therapies at temporally spaced apart times and/or with different analytes.

Other embodiments may allow improved individualized treatment protocols based on an in vivo detected uptake, trapping and/or other desired response (over a selected time) of a non-therapeutic dose of a drug, typically evaluated before and proximate in time to the delivery of the therapeutic dose) to predict the response of the subject to a therapeutic dose of a drug in advance of administration thereof. Such pre-delivery assessment capability may allow an improved patient customized selection of chemical or treatment drug, reducing unnecessary ineffective administration of cytotoxic agents, which are unlikely to be clinically effective. Thus, embodiments of the present invention can identify, by measuring detected fluorescence associated with the uptake and/or retention of a fluorescent analyte, the sensitivity or receptiveness of a tumor for a particular treatment, proximate in time to the planned delivery or administration of same. In addition, the data can be used to determine when a subsequent therapy should be administered, based on the uptake or retention or non-retention or decrease in the therapeutic analyte at the target site. Such data may allow a customized treatment plan rather than the delivery of treatments based on established standards.

Other embodiments gather data during a treatment cycle and evaluate it to determine the likely clinical efficacy based on the detected kinetic activity data.

Certain embodiments of the present invention are directed to methods for determining the in vivo clinical efficacy of a treatment in a subject. The method can include the steps of: (a) positioning a sensor in tissue in a region of interest in the body; (b) administering a fluorescent analyte to a subject; (c) detecting in vivo from the implanted sensor a signal corresponding to the fluorescence emitted from the analyte in the region of interest in the subject; (d) relaying the signal to a location external of the subject's body; and (e) monitoring the (relayed) signal over time to determine the response of the subject to the administered fluor-analyte to predict or assess at least one of the in vivo clinical efficacy of a selected treatment and/or the metabolic activity in the region of interest.

In particular embodiments where the fluor-analyte is a fluor-labeled analyte, the fluor-labeled analyte may be a fluorescently fluor-labeled version of a non-labeled corresponding drug or antibody that is undergoing pharmacokinetic/pharmacodynamic evaluation in clinical or pre-clinical drug trials (or other drug development testing). In other embodiments, the labeled analyte may be an analog of a chemotherapeutic agent for cytotoxic cancer treatment.

Other embodiments of the present invention are directed to a detection system for detecting in vivo fluorescence emitted from a systemically and/or locally administered fluorescent analyte. The system includes at least one fluor-sensor configured for in vivo operation. The sensor is configured to generate excitation light (optical radiation) and to detect fluorescence emitted from the labeled analyte or its biochemical constituents, in or proximate targeted localized tissue in the body. The sensor is configured to repetitively excite and then, detect emitted fluorescence, at least intermittently, over a period of time extending from at least about 0.25-24 hours, and typically between at least about 0.25-48 hours. In certain embodiments of the present invention, the evaluation period or data acquisition period may be performed over a period as small as several seconds or as long as several weeks to a month or more.

The evaluation period can be proximate in time to and at least before each of a plurality of planned therapeutic treatments that are administered temporally separate from each other. The system also includes a processor operably associated with (each of) the at least one sensor. The processor is configured to receive signal data associated with the detected fluorescence from the sensor. The processor includes computer program code for monitoring selected in vivo parameters associated with time-dependent measurement profile and/or the uptake and/or retention of the fluorescent analyte in the targeted localized tissue.

Yet other embodiments of the present invention are directed to computer program products for evaluating an individual's response to a planned cancer treatment regimen, the computer program product comprising a computer readable storage medium having computer readable program code embodied in the medium. The computer-readable program code comprising: (a) computer readable program code for receiving a first measurement of fluorescence detected in vivo in localized tissue at a target site in the body of a subject, the detected fluorescence corresponding to in vivo fluorescence emitted from a fluorescent analyte administered to the subject; (b) computer readable program code for receiving a second measurement of the in vivo fluorescence emitted from a fluorescent analyte detected in the localized tissue after the first measurement and (c) computer readable program code for generating a time-dependent measurement profile for evaluating selected parameters associated with at least one of the uptake and/or retention of the fluorescent analyte in the localized tissue of the subject based on the first and second measurements.

In other embodiments, the computer program code can be configured to obtain third and fourth measurements (or more measurements).

Other embodiments are directed to computer program products and methods for quantifying the amount (dose) of a gene therapy agent delivered to tissue in a target local site in the body of a subject in response to a treatment. The program product can include computer readable program code for (a) receiving data associated with fluorescence detected in vivo at a local target site in the body of a subject, (b) computer readable program code for generating a time-dependent measurement profile of the detected fluorescence at the local site; and (c) computer readable program code for evaluating the amount of gene therapy agent delivered to the local site based on the time-dependent measurements.

Certain embodiments are directed to methods for determining the in vivo clinical efficacy of a treatment in a subject. The method includes: (a) positioning at least one sensor in tissue in a region of interest in the body; (b) administering a fluorescent analyte to a subject; (c) emitting at least one excitation light signal from the at least one sensor to tissue proximate the at least one sensor; (d) detecting in vivo from the at least one sensor a signal corresponding to the fluorescence in the region of interest in the subject responsive to the administering step; (e) relaying the signal to a location external of the subject's body; and (f) monitoring the signal over time to determine the localized fluorescence response of the subject to the administered analyte.

In particular embodiments, the excitation light is able to penetrate tissue that is up to about 20 mm away, and wherein the fluor-label has an excitation wavelength of between about 630-660 nm that generates fluorescence response wavelengths of between about 665-695 nm. In certain embodiments of the present invention, the label has an excitation wavelength of from about 400 to about 660 nm that generates fluorescence response wavelengths of between about 400 to about 695 nm.

Other embodiments are directed to methods of evaluating a subject. The methods include: (i) administering a fluorescent analyte to a subject; (ii) repetitively emitting excitation light from an implanted sensor over a desired monitoring period; (iii) detecting fluorescence intensity in response to the excitation light using the implanted sensor that outputs the excitation light; and (iv) using data associated with the detected fluorescence intensity to perform at least one of: (a) calculate the concentration or dose of the fluorescent analyte received proximate to the implanted sensor site; (b) evaluate the pharmacodynamic and/or pharmacokinetic activity of the analyte; (c) confirm Ab attachment to a tumor site; (d) monitor a non-target site to confirm it is not unduly affected by a therapy; (e) monitor for changes in cellular properties; (f) use a calculated dose or concentration data to adjust or customize a therapeutic amount of a therapeutic agent administered to the subject; (g) confirm micelle concentration at a target site and then stimulate toxin release based on the confirmation; and (h) monitor for the expression of a protein produced from a gene therapy modification.

In particular embodiments, the intensity of the excitation signals emitted to the localized tissue can be varied in a predetermined manner to generate optical profiling data of the response of the tissue proximate the sensor.

Other embodiments are directed to detection systems for detecting fluorescence in a subject associated with an internally administered analyte. The system includes: (a) at least one fluorescence sensor configured for in vivo operation, the at least one sensor being configured to emit an excitation light signal and to detect fluorescence from a fluorescent analyte in localized target tissue in the body in response to the emitted excitation light signal, at least intermittently, over a period of time extending for at least about 24 hours after administration of a fluorescent analyte; and (b) a processor operably associated with the at least one sensor configured to direct the output of the excitation signal and to receive fluorescence intensity signal data associated with the detected fluorescence from the at least one sensor. The processor includes computer program code for monitoring intensity over time associated with one or more of the uptake and retention of the analyte in the targeted localized tissue at a plurality of points in time over at least one monitoring period.

Still other embodiments are directed to implantable fluorescence sensors. The sensors include: (a) an implantable elongated substantially cylindrical sensor body; (b) a cylindrical optical filter formed over the outer surface of the elongate sensor body; (c) at least one excitation light source held in the sensor body configured to generate excitation light from the sensor at a predetermined wavelength of interest having a power of between about 1-20 mW; and (d) at least one detector held in the sensor body configured to detect fluorescence at predetermined wavelengths of interest. The sensor is configured to be intermittently operated at plurality of sampling intervals over a monitoring period of interest.

Still other embodiments are directed to computer program products for evaluating a subject's in vivo response to a fluorescent analyte. The computer program product includes a computer readable storage medium having computer readable program code embodied in the medium. The computer-readable program code includes: (a) computer readable program code for directing the emission of at least one excitation light signal from a sensor held in a subject at a local target site in the body of a subject at depths from about 1 cm up to about 25 cm, or from about 5 cm to about 20 cm, in vivo a plurality of times during a monitoring period having a duration of at least about 1 hour; (b) computer readable program code for serially receiving fluorescence intensity count data detected in vivo in tissue proximate the target site from the sensor over time, the detected intensity data corresponding to fluorescence generated from tissue having a fluorescent analyte that is administered internally therein responsive to exposure to the excitation light; and (c) computer readable program code for generating a time-dependent measurement profile for evaluating selected parameters associated with at least one of the signal intensity, concentration, uptake and retention of the labeled analyte in the localized tissue of the subject.

BRIEF DESCRIPTION OF THE FIGURES

FIG. 5A was taken with a 647 nm line of a laser and illustrates primary antibody labeling. FIG. 5B was taken at 568 nm and illustrates secondary antibody labeling.

DESCRIPTION OF EMBODIMENTS OF THE INVENTION

Figure 1A:
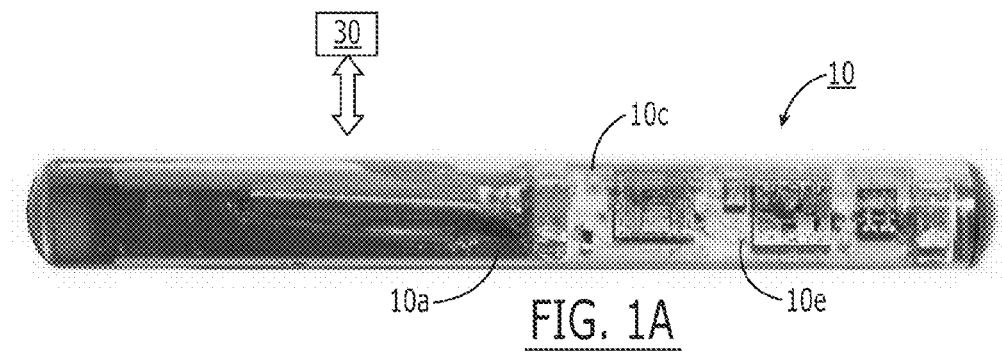
FIG. 1A is an enlarged screen printout of an implantable sensor according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the Figures, certain layers, components or features may be exaggerated for clarity, and broken lines illustrate optional features or operations unless specified otherwise. In addition, the sequence of operations (or steps) is not limited to the order presented in the claims unless specifically indicated otherwise. Where used, the terms "attached", "connected", "contacting", "coupling" and the like, can mean either directly or indirectly, unless stated otherwise. The term "concurrently" means that the operations are carried out substantially simultaneously.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer, processor (such as a digital signal processor), or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

Generally described, in certain embodiments, the proposed device and systems can be used to obtain data and/or measure or monitor the emission of fluorescence from a fluorescent analyte. The term "fluorescent analyte" includes a fluorescently labeled analyte, a naturally fluorescent analyte and/or an analyte that exhibits fluorescence when introduced or internally administered to a subject (via induced or natural biochemical activity). As used herein "internally administered" refers to introducing an analyte or substance, systemically and/or locally, into a subject by whether ingesting the analyte, topically applying the analyte, providing the analyte intravenously, inhaling the analyte, injecting the analyte and the like. Although embodiments of the present invention are primarily discussed herein with respect to fluorescently labeled analytes (fluor-labeled analytes), other embodiments of the present invention are not limited to this configuration. As discussed above, naturally fluorescent analytes and/or analytes that exhibit fluorescence when introduced (ingested, inhaled, intravenous, injection, topical) to a subject may also be used without departing from the teachings of the present invention.

The term "fluor-labeled analyte" is used interchangeable with "fluorescently labeled analytes" and includes, but is not limited to, fluorescently labeled antibodies, antigens, nucleic or amino acids, other fluorescently labeled endogenous or naturally occurring substances, compounds or molecules of suitable molecular size and/or their derivatives, metabolites, or constituents, as well as fluorescently labeled exogenous substances and/or molecules such as pharmaceutical drugs or derivatives thereof, and the like, as well as combinations of the above.

The term "naturally fluorescent analytes" refers to substances and/or molecules that are not "fluor-labeled" as discussed above, as these analytes have a natural fluorescent component. Naturally fluorescent analytes may include, but are not limited to, camptothecin analogs (CAMPTOTHECIN) and/or adriamycin (DOXORUBICIN). Finally, analytes that exhibit fluorescence when internally administered or introduced to a subject are analytes that may not have a fluorescent component outside the body, but become fluorescent in response to in vivo biochemical activity. These types of analytes may include, but are not limited to CATHEPSIN B, CATHEPSIN D, MMP-2, CATHEPSIN K, THROMBIN, CASPASE 3 and the like.

The light emitted from the fluorescent analyte can be detected in vivo from tissue in target or localized region(s) in the body. This in vivo detected and monitored fluorescence can provide information on one or more of the metabolic activity in the localized region, tissue, or cells, the pharmacokinetics and/or pharmacodynamics of a corresponding non-labeled analyte or substance, the uptake and/or the retention of certain chemotherapeutic drugs in the localized region or tissue, and/or a substantially real-time and/or kinetic analysis of the biological status, metabolism and/or proliferation of malignant and/or normal cells in the localized tissue or region at desired points in time. In embodiments of the present invention that use fluor-labeled analytes, the fluor-labeled version of the non-labeled (i.e., "parent") analytes can be formulated to have the same or substantially similar pharmacological or biochemical activity as the corresponding parent analyte.

Such systems and methods can be used to obtain and/or analyze data or physical quantities from the living body to provide intermediate data that may be provided to a clinician or researcher for further consideration. The detection can be carried out using a plurality of sensors located at multiple sites about a region of interest or at a plurality of different spaced apart sites in the body. The systems, methods, and operations of the present invention may be carried out to monitor, for longer times over conventional systems, the biological or physiological impact of a selected therapy (or combinations of therapies) on a target disease, disorder, or condition of the body (pharmacodynamics) in addition to the in vivo levels, activity, retention, uptake, delivery, etc., of therapeutic agents (pharmacokinetics).

Certain embodiments of the systems and methods of the present invention may be used with any analyte which can be fluorescently labeled and of sufficient molecular size, including, but not limited to, as noted above, endogenous material that can be labeled and re-introduced to the subject, or exogenous material. As also noted above, suitable labeled analytes can include labeled versions of nuclides, pharmaceuticals and derivatives thereof, antibodies, antigens, proteins, peptides, amino acids, nucleic acids, metabolites and derivatives thereof. The labeled analyte may be a genetically engineered, synthetic, or naturally occurring substance, which has a site-specific or tumor or tissue specific delivery target, a differentiation antigen, or an analyte which can be activated upon delivery to a particular region or tissue or which can otherwise be locally "activated" or targeted. The labeled analyte may be selected based on its presence or expression, i.e., a labeled marker associated with a disease or cancer in the region or at the targeted site, such as an over or under expression of an antigen, antibody, peptide, protein, enzyme, amino acid or other endogenous analyte, or other genome or phenotype(s) criteria or behavior. Thus, it is contemplated that active fluorescence monitoring for dynamic amounts of the marker or antigen expression can provide clinically valuable internal real time or dynamic information about cellular activity.

In certain embodiments, subjects can be "pre-tested" or evaluated using analytes that are fluorescently pre-labeled before they are administered to a subject. The term "pre-labeled" means that the analyte is labeled external of the subject and then administered to the subject so that the fluor-labeled analyte or constituent thereof travels to a target site and/or cells. It is noted that as used herein, the term "fluor-labeled analyte" includes biochemical constituents thereof in the body. The internal response can then be evaluated using the pre-labeled analyte in the subject's in vivo biosystem as it is exposed to the same biomolecules and physiochemical environment as the tumor or target treatment region and this may influence the analyte's behavior in the body (such as uptake and/or treatment efficacy).

Certain embodiments of the present invention can be used to screen or determine what phenotypes are likely to be responsive to a selected therapy and/or to evaluate phenotypic responses to a selected analyte. This data can be used for drug screening to help identify those subjects who may experience a therapeutic benefit over other segments of the population (such as for drug screening) and/or to customize therapy and drug selection for a particular patient.

In yet other embodiments, operations can be carried out to evaluate the cytostatic versus cytotoxic effect that a cancer therapy or analyte has, over time, on a target cell group or tumor site. Additionally, a first generation of cells treated with a gene therapy may produce a change in cellular production (such as reduced or increased production of a certain protein). Operations of the present invention can be carried out over time to determine whether the therapy remains effective in the second, third or other subsequent generation of cells to determine if the gene therapy has been sustained in the body (such as by monitoring for the continued presence or level of the protein or other cellular production).

Examples of marker or expression-based evaluation of antigens/antibodies (which may be labeled) include those used in cancer evaluation and/or treatment. Examples of tumor-associated antigens of interest may include the CD-20 antigen (on B lymphocytes) for which treatment may include agents having antibodies to the CD-20 antigen and human epidermal growth factor (HER2) associated with some breast tumors. It is noted that HERCEPTIN may be fluorescently labeled and is currently approved for HER2 breast cancer treatment.

It is contemplated that other biomaterials may also be suitable to carry out operations of the present invention. Examples of potentially suitable biomaterials may include, but are not limited to, mixed cultures containing tumor cells and blood-derived lymphocytes (which may be from the patient him or herself) to produce cytolytic T lymphocytes (CTL) (or CTL clones or autologous CTL), that lyse the autologous tumor cells (which may be used in connection with melanoma, renal, bladder, head and neck carcinomas, non-small lung cancer, and the like). Other potential antigens/antibodies of interest include MAGE-1, MAGE-3, BAGE, GAGE-1, GAGE-3, Camptothecin analogs, epidermal growth factor (i.e. Vascular Endothelial Growth Factor (VEGF)) and angiogenic factors. See, e.g., UCL Christian de Duve Institute of Cellular Pathology, *Ludwig Institute For Cancer Research*, URL lcp.ucl.ac.be/report95/licr95.html.

In any event, the labeled analyte may be combined with other substances and formulated for the desired delivery (injection, intravenous, subcutaneous, etc. . . . ) to produce the desired composition and/or bolus. In certain embodiments, the fluor-analyte can be formulated into a liquid solution. The solution can be formulated to dilute the concentration of the labeled constituent or ingredient or to provide other desired biocompatible materials.

The term "subject," according to the present invention, includes subjects belonging to the animal kingdom, and are preferably mammalian subjects (e.g., humans, canines, felines, bovines, caprines, ovines, equines, rodents, porcines, and/or lagomorphs), and more preferably are human subjects.

The term "tissue" includes all substances in the body, e.g., an aggregation of morphologically similar cells and intercellular matter performing one or more functions in the body (such as, but not limited to, muscle, arteries, veins, vessels, tissue, bone, bone marrow, and the like) as well as serum, interstitial fluid or liquid. The liquid or fluid detection may be more typically measured with a fiber version of a detection or sensor probe rather than a non-fiber version of the sensor.

In certain embodiments, the analyte is a therapeutic pharmaceutical drug or antibody that is configured to treat a selected physiologic or biologic condition, impairment, or disease. The fluorescent label can be selected or formulated to be substantially transparent so that the non-labeled version and the labeled version of the same analyte has substantially the same biochemical activity in the body and/or so that the labeled version does not interfere with the intended therapeutic, physiologic, or biologic reaction in the body. As such, the labeled version of the analyte (or drug or antibody) can be such that the labeled version biologically functions or is biochemically processed in substantially the same manner as a corresponding non-radiolabeled version. In certain embodiments, the label is biocompatible (non-toxic) at the concentrations used for evaluation and does not inhibit or interfere with the natural breakdown or reaction of the analyte and/or its constituents in the body.

A listing of select references is difficult due to the number of strategies developed for this sort of investigation. It is illustrative to refer to the catalogs of vendors of fluorescence kits (see, e.g., URL http://molecularprobes.com or products from Molecular Probes, Inc., located in Eugene, Oreg.) for examples of fluor-labels and/or tests already developed. It is known to those of skill in the art that some fluors are cytotoxic, but many are safe at fairly high concentrations. Thus, in vivo administration of fluor-labeled analytes for therapeutic or theragnostic evaluation is viable. Examples of different types of fluor-labels or fluor-analytes include, but are not limited to, reactive dyes and other novel fluorophores, enzyme-labeled fluorescence (ELF), high-sensitivity nucleic acid stains, high-sensitivity protein stains, organelle stains, fluorescent microspheres for biological applications, fluorogenic enzyme substrates, cell viability assays, and ion indicators. Furthermore, molecules smaller than fluorophores may also be labeled as long as the binding site is not obstructed.

Table 1 lists examples of issued United States patents describing fluorescent labels or related tests and devices. The contents of each of the patents listed in Table 1 is hereby incorporated by reference as if recited in full herein.

TABLE 1

| Pat. No. | Patent Title |
| --- | --- |
| U.S. Pat. No. 4,774,339 | Chemically Reactive Dipyrrometheneboron Difluoride Dyes |
| U.S. Pat. No. 4,945,171 | Xanthene Dyes Having a Fused [C] Benzo Ring |
| U.S. Pat. No. 5,132,432 | Chemically Reactive Pyrenyloxy Sulfonic Acid Dyes |
| U.S. Pat. No. 5,187,288 | Ethenyl-Substituted Dipyrrometheneboron Difluoride Dyes and Their Synthesis |
| U.S. Pat. No. 5,908,148 | Lipophilic Fluorescent Glycosidase Substrates |
| U.S. Pat. No. 5,227,487 | Certain Tricyclic and Pentacyclic-Hetero Nitrogen Rhodol Dyes |
| U.S. Pat. No. 5,242,805 | Long Wavelength Lipophilic Fluorogenic Glycosidase Substrates |
| U.S. Pat. No. 5,248,782 | Long Wavelength Heteroaryl-Substituted Dipyrrometheneboron Difluoride Dyes |
| U.S. Pat. No. 5,262,545 | Fluorescent Chloramphenicol Derivatives for Determination of Chloramphenicol Acetyltransferase Activity |
| U.S. Pat. No. 5,274,113 | Long Wavelength Chemically Reactive Dipyrrometheneboron Difluoride Dyes and Conjugates |
| U.S. Pat. No. 5,314,805 | Dual-Fluorescence Cell Viability Assay Using Ethidium Homodimer and Calcein AM |
| U.S. Pat. No. 5,316,906 | Enzymatic Analysis Using Substrates That Yield Fluorescent Precipitates |

TABLE 1-continued

| Pat. No. | Patent Title |
| --- | --- |
| U.S. Pat. No. 5,321,130 | Unsymmetrical Cyanine Dyes With Cationic Side Chains |
| U.S. Pat. No. 5,326,692 | Fluorescent Microparticles With Controllable Enhanced Stokes Shift |
| U.S. Pat. No. 5,338,854 | Fluorescent Fatty Acids Derived from Dipyrrometheneboron Difluoride Dyes |
| U.S. Pat. No. 5,362,628 | Fluorescent Haloalkyl Derivatives of Reporter Molecules Well Retained in Cells |
| U.S. Pat. No. 5,364,764 | Fluorescent Chloramphenicol Derivatives for Determination of Chloramphenicol Acetyltransferase Activity |
| U.S. Pat. No. 5,405,975 | Fluorescent Ion-Selective Diaryldiaza Crown Ether Conjugates |
| U.S. Pat. No. 5,410,030 | Dimers of Unsymmetrical Cyanine Dyes Containing Pyridinium Moieties |
| U.S. Pat. No. 5,433,896 | Dibenzopyrrometheneboron Difluoride Dyes |
| U.S. Pat. No. 5,436,134 | Cyclic-Substituted Unsymmetrical Cyanine Dyes |
| U.S. Pat. No. 5,437,980 | Phenanthridium Dye Staining of Nucleic Acids in Living Cells |
| U.S. Pat. No. 5,442,045 | Biological Conjugates of Fluorescent Rhodol Dyes |
| U.S. Pat. No. 5,443,986 | Enzymatic Analysis Using Substrates That Yield Fluorescent Precipitates |
| U.S. Pat. No. 5,445,946 | Viability Stains for Yeast and Other Fungi |
| U.S. Pat. No. 5,451,663 | Long Wavelength Chemically Reactive Dipyrrometheneboron Difluoride Dyes and Conjugates |
| U.S. Pat. No. 5,453,517 | Reactive Derivatives of BAPTA Used to Make Ion-Selective Chelators |
| U.S. Pat. No. 5,459,268 | Xanthylium Dyes That Are Well Retained In Mitochondria |
| U.S. Pat. No. 5,459,276 | Benzazolylcoumarin-based Ion Indicators For Heavy Metals |
| U.S. Pat. No. 5,501,980 | Benzazolylcoumarin-based Ion Indicators |
| U.S. Pat. No. 5,514,710 | Photocleavable Derivatives of Hydroxypyrenesulfonic Acids |
| U.S. Pat. No. 5,516,864 | Fluorescent Ion-Selective Diaryldiaza Crown Ether Conjugates |
| U.S. Pat. No. 5,534,416 | Fluorescent Viability Assay Using Cyclic-Substituted Unsymmetrical Cyanine Dyes |
| U.S. Pat. No. 5,545,535 | Fluorescent Assay for Bacterial Gram Reaction |
| U.S. Pat. No. 5,573,909 | Fluorescent Labeling Using Microparticles With Controllable Stokes Shift |
| U.S. Pat. No. 5,576,424 | Haloalkyl Derivatives of Reporter Molecules Used to Analyze Metabolic Activity in Cells |
| U.S. Pat. No. 5,582,977 | Dimers of Unsymmetrical Cyanine Dyes |
| U.S. Pat. No. 5,616,502 | Non-specific Protein Staining Using Merocyanine Dyes |
| U.S. Pat. No. 5,635,608 | Alpha-Carboxy Caged Compounds |
| U.S. Pat. No. 5,648,270 | Methods of Sensing with Fluorescent Conjugates of Metal-Chelating Nitrogen Heterocycles |
| U.S. Pat. No. 5,656,449 | Neutral Unsymmetrical Cyanine Dyes |
| U.S. Pat. No. 5,658,751 | Substituted Unsymmetrical Cyanine Dyes with Selected Permeability |
| U.S. Pat. No. 5,686,261 | Xanthylium Dyes that are Well Retained in Mitochondria |
| U.S. Pat. No. 5,696,157 | Sulfonated Derivatives of 7-Aminocoumarins |
| U.S. Pat. No. 5,719,031 | Dye Labeled Polymers as Reagents for Measuring Polymer Degradation |
| U.S. Pat. No. 5,723,218 | Dipyrrometheneboron Difluoride Labeled Fluorescent Microparticles |
| U.S. Pat. No. 5,773,227 | Bifunctional Chelating Polysaccharides |
| U.S. Pat. No. 5,773,236 | Polyhaloaryl-Substituted Reporter Molecules |
| U.S. Pat. No. 5,786,219 | Microspheres with Fluorescent Spherical Zones |
| U.S. Pat. No. 5,798,276 | Reactive Derivatives of Sulforhodamine 101 with Enhanced Hydrolytic Stability |
| U.S. Pat. No. 5,830,912 | Derivatives of 6,8-Difluoro-7-hydroxycoumarin |
| U.S. Pat. No. 5,846,737 | Conjugates of Sulforhodamine Fluorophores with Enhanced Fluorescence |
| U.S. Pat. No. 5,863,753 | Chemically Reactive Unsymmetrical Cyanine Dyes and their Conjugates |
| U.S. Pat. No. 5,869,689 | Stains for Acidic Organelles |
| U.S. Pat. No. 5,872,243 | Novel Caged Nucleotides |
| U.S. Pat. No. 5,888,829 | Photolabile Caged Ionophores |
| U.S. Pat. No. 6,004,536 | Lipophilic Cyanine Dyes with Enhanced Aqueous Solubility |
| U.S. Pat. No. 6,005,113 | Long Wavelength Dyes for Infrared Tracing |
| U.S. Pat. No. 6,013,802 | Fluorescent Conjugates of Metal-Chelating Nitrogen Heterocycles |
| U.S. Pat. No. 6,130,101 | Sulfonated Xanthene Derivatives |
| U.S. Pat. No. 6,162,931 | Fluorinated Xanthene Derivatives |
| U.S. Pat. No. 6,229,055 | Synthesis of Fluorinated Xanthene Derivatives |
| U.S. Pat. No. 6,265,179 | Detection of Phosphate using Coupled Enzymatic Reactions |
| U.S. Pat. No. 6,291,203 | Cyanine Dyes that Stain Cells and Mitochondria |
| U.S. Pat. No. 6,316,267 | Luminescent Protein Stains and Their Method of Use |
| U.S. Pat. No. 6,323,337 | Quenching Oligonucleotides |

TABLE 1-continued

| Pat. No. | Patent Title |
| --- | --- |
| U.S. Pat. No. 6,323,186 | Phosphate-Bound Polyazaindacene Derivatives of Nucleotides |
| U.S. Pat. No. 6,329,205 | Detection Method using Luminescent Europium-Based Protein Stains |
| U.S. Pat. No. 6,399,392 | Xanthene Dyes and their Application as Luminescence Quenching Compounds |

This application describes embodiments of implantable sensors and platform devices (devices) used to probe fluorescently labeled analytes in vivo as described above. In particular embodiments, the analytes are exogenous in origin, e.g., antibodies delivered for cancer therapy and/or used for gene therapy or other uses. As described above, methods, sensors, devices, systems and computer program products of the present invention can operate to monitor the internal localized dose, dynamic uptake and/or retention of the therapy in the localized tissue over a time period of interest, of a therapeutic antibody received at and taken up in target tissue and/or to monitor the expression of proteins that provide indications of cellular status.

The implantable sensor can be configured to be telemetrically operated and used as a monitor of internal activity (such as cellular processes) associated with cancer cells before, during and/or after an active treatment, and/or to evaluate a gene therapy. Additional description of a telemetrically operated implantable sensor unit and reader is provided in U.S. Pat. No. 6,402,689 and co-pending U.S. patent application Ser. No. 10/127,207, the contents of which are incorporated by reference as if recited in full herein.

As described herein, methods and devices provided by the instant invention have demonstrated the ability to follow the progress of a labeled antibody (HERCEPTIN) in vivo and dynamically in a nude mouse with a human breast tumor xenograft. The measurements were made using a fiber-optic based device. Therapeutic cancer antibodies generally have time courses of 2-4 days in the body after administration.

Embodiments of the present invention provide a fully implantable sensor capable of making the same type of measurement. The methods and devices can generate pharmacokinetic "PK" profiles to monitor the impact of certain therapies, thus providing valuable information to the clinician on clinical effect. In certain embodiments, the therapy can be a cytotoxic agent or antibody selected because of the relatively large size of the biomolecules forming the agent or antibody, allowing them to be labeled with fluors without altering their pharmacokinetic properties.

Specifically, fluorescent tags are available to delineate antigens expressed on cell membrane surfaces, the density of which might change in time. For example, generally described, HERCEPTIN works by attaching to transmembrane proteins, but the density is generally assumed to be fixed in time. The expression of such antigens on the membrane or in the cell can signal significant events that have import in tumor control (e.g., onset of metastatic potential, cell cycle status, etc.). Fluor-labels are also available that will show the onset of apoptosis, programmed cell death that signals the end stage of most cancer therapies. In short, embodiments of the present invention can be used to monitor the internal localized dose of a therapeutic antibody and/or the expression of proteins that provide indications of cellular status.

Similar monitoring techniques have value in genetic therapy applications. One problem in clinical gene therapy is the difficulty in perpetuating the effects of an alteration into successive generations of cells. In human patients, the failure or diminution of genetic therapy may only become clear by repeated biopsy or the onset of a relapse in clinical symptoms. The ability to monitor gene expression in vivo on a chronic basis may be an important tool by which advances in therapy might take place. "Chronic" basis means a duration of at least 2-4 weeks. Typically, the implantable sensor is configured to be implanted for 4-6 weeks, 6-12 weeks, or for the duration of a therapy (such as 3-6 months or longer). The devices described herein can be beneficial in this endeavor.

Some embodiments according to the present invention may be used in two primary application areas: pharmacokinetic and pharmacodynamic fluorescence monitoring. In the first, a labeled molecule is assayed quantitatively and dynamically at a particular site, for example in and around a tumor. Pharmacodynamic fluorescence refers to the activation of a fluorophore used as a reporter (e.g., activation as a result of a certain protein expression on a cell membrane). Pharmacokinetic fluorescence generally addresses dosing and specificity of a given therapeutic entity. Pharmacodynamic fluorescence generally addresses the effects of that therapy on cellular processes. The advantage in creating an in vivo probe is that acute and chronic measurements of both types of kinetics may now be possible.

Antibody (Ab) based therapies are now entering the clinical market. Products like HERCEPTIN (trastuzumab, Genetech) and RITUXAN (rituximab, IDEC) are showing great promise alone and in combination with other therapies. For example with non-Hodgkin's lymphoma, RITUXAN is given in combination with yet another new Ab-based radioimmunotherapeutic, Zevalin (ibritlmomab tiuxetan, IDEC), which carries a powerful beta emitter, Y-90, to irradiate targeted B cells. An issue common to all of these products is proper dosing. In the case of HERCEPTIN, a candidate patient is first tested for the level of expression of the HER2/neu (or c-erbB2) gene. Roughly 25% of women have levels of expression high enough to warrant use of the therapy. Zevalin is currently given with In-111 in a "tracer" mode to look at biodistribution and clearing before setting the final dose with the Y-90 variety. Determining a proper dosage for a particular patient is often a poorly defined endeavor.

With antibodies in particular, fluorescent labels or tags are attractive markers because of the large molecular weights involved. That is, it's possible to identify fluorophores that, when conjugated to the Ab, will not inhibit and/or unduly affect the pharmacokinetics of the therapeutic agent. In fact, such studies are often done as a part of the normal development of the therapeutic product. By labeling the therapeutic agent in this way, the concentration can then be assessed at the site of action and the kinetics of binding and release can be studied if one has an in situ fluorescence monitor. The present invention provides an in situ fluorescence monitor that is adapted to sense at a relatively wide range of clinically significant depths in the body of a subject.

Quantification and kinetics, as described above, are targets for an in vivo probe. They address dosing. If the therapeutic compound fails, the next question of interest is why. Perhaps the target cells received the prescribed dose but have become resistant. This could be termed pharmacodynamic failure. In this situation it would be attractive to employ fluorescence activation in response to a cellular event: gene or protein expression, onset of apoptosis, etc.

In some embodiments of the present, information can be gathered from individual cells, but may be particularly suitable for monitoring regions, clusters, volumes, and/or areas of tissue, which can be on the order of about several millimeters or more in size.

Examples of chemotherapeutic pharmaceutical products, which can be formulated with a fluor-label, include antineoplastics such as alkylating agents, nitrogen mustards, nitrosureas, antibiotics, hormonal antagonists or androgens, antiandrogens, antiestrogens, estrogen/nitrogen mixtures, estrogens, gonadotropin releasing hormones, immunomodulators, and other appropriate therapeutic agents. Other products not specifically listed may also be used as contemplated by embodiments of the present invention. Table 2 lists examples of products, which may be suitable for fluor-labeling or monitored for effect using a fluor-probe, such as for cancer treatments, according to embodiments of the present invention.

TABLE 2

| Agent | Manufacturer |
| --- | --- |
| A. Alkylating agents | |
| 1. Myleran | GlaxoSmithKline (Glaxo) |
| 2. Paraplatin, platinol | Bristol Myers Squibb (BMS) |
| 3. Temodar | Schering |
| B. Nitrogen Mustards | |
| 1. Alkeran | Glaxo |
| 2. Cytoxan | BMS |
| 3. Ifex | BMS |
| 4. Leuderan | Glaxo |
| C. Nitrosureas | |
| 1. BCNU | BMS |
| 2. CCNU | BMS |
| 3. Gliadel wafer | Aventis |
| D. Antibiotics | |
| 1. Adriamycin | Pharmacia & Upjohn |
| 2. Blenoxane | BMS |
| 3. Idamycin | Pharmacia & Upjohn |
| 4. Mithracin | Bayer |
| 5. Mutamycin | BMS |
| 6. Novantrone | Immunex |
| 7. Rubex | BMX |
| 8. Fludara | Berlex |
| 9. FUDR | Roche |
| 10. Thioguanine | Glaxo |
| 11. Xeloda | Roche |
| E. Hormonal Antagonists | |
| 1. Nilandron | Aventis |
| 2. Teslac | BMS |
| F. Antiandrogens | |
| 1. Casodex | AstraZenaca |
| 2. Eulexin | Shering |
| G. Antiestrogens | |
| 1. Arimedex | AstraZenaca |
| 2. Aromasin | Pharmacia |

TABLE 2-continued

| Agent | Manufacturer |
| --- | --- |
| 3. Femara | Novartis |
| 4. Nolvadex | AstraZenaca |
| H. Estrogen/Nitrogen mixture | |
| 1. Emcyt | Pharmacia |
| I. Estrogens | |
| 1. Estinyl | Schering |
| J. Gonadotroopin Releasing Hormones | |
| 1. Lupron | TAP |
| 2. Zoladex | AstraZeneca |
| K. Progestins | |
| 1. Megace | BMS |
| L. Immunomodulators | |
| 1. Ergamisol | Jansen |
| M. Antibody Therapies | |
| 1. Herceptin | Genetech |
| 2. Rituxan | Genetech, IDEC |
| 3. Zevalin | IDEC |
| 4. Avastin | Genetech |
| 5. ABX-EFG | Abgenix |
| 6. Bexxar | Corixa |
| 7. Campath | Millenium and ILEX Partners, LP |
| 8. Erbitux | Bristol Myers Squibb |
| 9. Myoltarg | Wyeth Ayerst |
| 10. Ontak | Seragen, Inc. |
| 11. Vascular Endothelial Growth Factor (VEGF) | Under Development |
| N. Non-Antibody Therapies | |
| 1. Gleevec/Glivec | Novartis |
| 2. Hycamtin | Glaxo Smithkline |
| 3. Taxol | Bristol Myers Squibb |
| O. Naturally Fluorescent Analytes | |
| 1. Camptothecin analogs | Under Development |
| 2. Adriamycin | Pharmacia & Upjohn Co. |
| P. Miscellaneous | |
| 1. Camptosar | Pharmacia |
| 2. DTIC | Bayer |
| 3. Etopophos | BMS |
| 4. Gemzar | Lilly |
| 5. Hydrea | BMS |
| 6. Intron A | Scherling |
| 7. Lysodren | BMS |
| 8. Navelbine | Glaxo |
| 9. Oncovin | Lilly |
| 10. Proleukin | Chiron |
| 11. Roferon A | Roche |
| 12. Taxon | BMS |
| 13. Taxotere | Aventis |
| 14. Velban | Lelly |
| 15. VePesid | BMS |

Table 3 includes exemplary analytes or compounds that could be assayed with fluorescence sensors according to some embodiments of the present invention. Some of the analytes listed in Table 3 are also included in Table 2, however, Table 3 may contain more details with respect to these analytes.

| DRUG TRADE NAME | DRUG | MANUFACTURER | USE |
|---|---|---|---|
| ANTIBODIES THAT MAY BE FLUORESCENTLY LABELED | | | |
| ABX-EGF | Epidermal Growth Factor (EGF) receptor inhibitors | Abgenix (under development) | Targets EGF receptor which is overexpressed in various cancers |
| Avastin | Bevacizumab | Genentech | Angiogenesis inhibitor |
| Bexxar | Tositumomab | Corixa | CD20 positive, follicular, non-Hodgkin's lymphoma |
| Campath | Alemtuzumab | Millenium and ILEX Partners, LP | Anti-CD52 antibody; B-cell chronic lympocytic leukemia |
| Erbitux | Cetuximab | Bristol Myers Squibb (under development) | Targeted anti-cancer therapy |
| Herceptin | Trastuzumab | Genentech | HER2 positive metastatic breast cancer |
| Mylotarg | Gemtuzumab ozogamicin | Wyeth Ayerst | CD33 positive acute myeloid leukemia |
| Ontak | Denileukin | Seragen, Inc. | CD25 positive IL-2 receptor in recurrent cutaneous T-cell lymphoma |
| Rituxan | Rituximab | Genentech, IDEC | Refractory, low-grade or follicular CD20 positive non-Hodgkin's lymphoma |
| Vascular Endothelial Growth Factor (VEGF) inhibitors | VEGF inhibitor analogs | Under development by various researchers | Inhibits VEGF |
| Zevalin | Ibritumomab tiuxetan | IDEC | Low-grade, follicular, or transformed B-cell non-Hodgkin's lymphoma |
| NON-ANTIBODY ANALYTES THAT MAY BE FLUORESCENTLY LABELED | | | |
| Gleevec/Glivec | Imatinib mesylate | Novartis | Chronic myelogenous leukemia |
| Hycamtin | Topotecan hydrocholoride (Camptothecin analog) | Glaxo Smith Kline | Inhibits topoisomerase I |
| Taxol | Paclitaxel | Bristol-Myers Squibb | Node-positive breast cancer |
| NATURALLY FLUORESCENT ANALYTES | | | |
| Adriamycin | Doxorubicin | Pharmacia & Upjohn Co. | Antibiotic, antitumor agent |
| Camptothecin analogs | Camptothecin analogs | Under development by various researchers | Inhibits topoisomerase I |

Figure 13A:
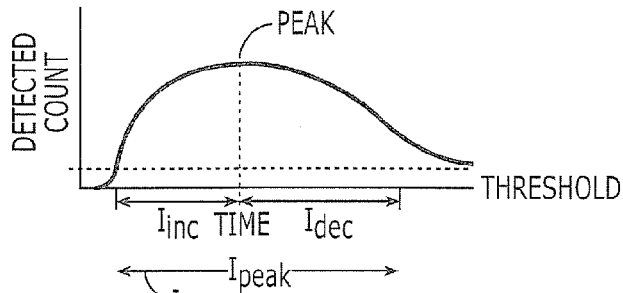
FIGS. 13A-13E are graphs of time-dependent measurement profiles of intensity over time according to embodiments of the present invention.

In certain embodiments, one or more time-dependent, and/or variable excitation intensity dependent profiles, can be generated, analyzed and/or monitored. FIGS. 13A-13E are examples of response profiles that can be generated of selected parameters or predictor variables and time-dependent profiles can be generated, analyzed or monitored. FIG. 13A illustrates that a profile of fluorescence intensity can be obtained and the time that the intensity remains above a threshold level can then be determined. In certain embodiments, the monitored response time or period can be individualized. That is, the response time can be based on how long measurements of detected fluorescence remain above a predetermined threshold value (the threshold value is represented by the broken line adjacent the X axis). In other embodiments, the response or monitoring period can be standardized and/or pre-determined (such as at desired intervals occurring over 1-3 hours, 24-48 hours or longer).

It will be understood that the response or monitoring periods discussed herein are provided for exemplary purposes only and that embodiments of the present invention should not be limited to these examples. For example, response or monitoring periods may be in the range of from about several seconds to weeks or months without departing from the scope of the present invention.

As shown, in FIGS. 13A, 13B, 13C and 13E, the fluorescence intensity can be detected over a period of time (t). The time at which the intensity level is above a particular value can be defined as the time during which the local tissue is able to uptake, trap, accumulate and/or retain the labeled analyte ($t_{trap}$). The particular value is shown as a threshold value (such as a value obtained in vitro or in vivo before delivery of the fluor-labeled analyte), but the value may be defined to a different desired relative or absolute value. In any event, the detected intensity may have a peak at a particular time in the response cycle ($t_{peak}$). In addition, the intensity may increase during a portion of the response cycle ($t_{inc}$) and decrease for a period of time thereafter ($t_{dec}$). The rate of increase or decrease or time to reach the peak or the lower threshold may also be calculated based on the monitored values. Further, the acceleration or deceleration or decay rate (either an average or at particular times during the monitored period) can be established.

One or a combination of parameters or appropriate predictor variables can be correlated or statistically evaluated to determine the impact on clinical outcome, dosage, or performance in the body. As such, the selected parameter can be predictive of a desired performance, response or status of the localized tissue in the subject (or in other embodiments of the delivery and/or the quantification of the amount of labeled substance actually delivered to the targeted treatment site).

For example, if a subject has a relatively long ligand binding time, such that it is able to retain the labeled Ab above a certain level for greater times (either absolute or relative) than previously or in comparable subjects or as established in clinical data, this capability may represent a positive predictive factor. Similarly, if the concentration decay rate is slow or the peak (or time to saturation) is reached later in the response cycle, this may also represent a positive predictive factor or that a favorable treatment response is indicated. Other examples include later uptake and/or a smaller decrease from a peak value after a representative time. For example, if the signal exhibits less than a predetermined percentage drop from peak or maximum fluor-intensity activity after a representative time (such as after about 1-24 or 48 hours after initiation of the administration of the labeled analyte to the subject), this may represent a favorable predictive factor.

Figure 13B:
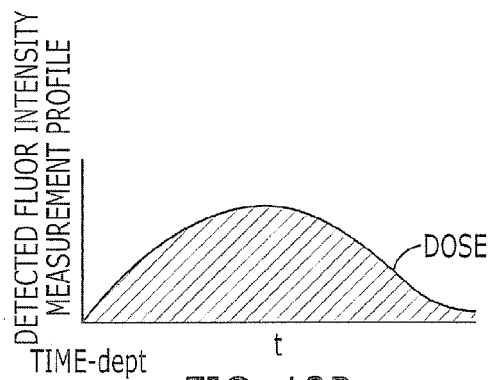
Figure 13C:
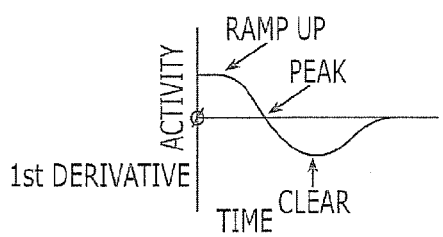

FIG. 13B illustrates that the area under the curve can be used to calculate the dose of labeled analyte received at the targeted site. The intensity response profile can be correlated to a priori data to define the delivered in vivo dose. The a priori data can be based on in vitro evaluations of samples. Other dose correlation or calculation means can also be employed. FIG. 13C illustrates that the signal can be monitored and then a (first) derivative mathematically taken to represent the rate of change of concentration over time associated therewith. For illustration, in the embodiment shown, the line shape of FIG. 13C corresponds to the derivative of the profile of FIG. 13A, albeit in a unitless manner without accounting for the amplitude values. The activity corresponds to the intensity count (C) over time (taken in pulsed excitation intervals as noted above). Other parameters and quantification or evaluation processing methods can be used depending on the particular application and information desired.

Figure 13D:
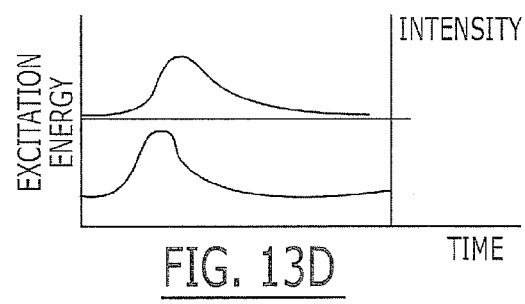
Figure 13E:
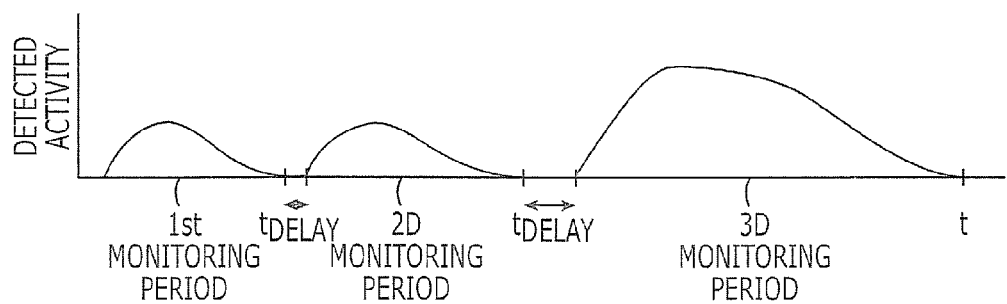

FIG. 13E illustrates that the system can obtain a plurality of different data sets, each corresponding to serially spaced monitoring periods. As shown, three different temporally separate response periods are monitored. The third response period is shown as having an increase in detected fluorescence intensity as may occur when an enhanced or favorable treatment is identified. These monitoring procedures can be performed prior to each therapeutic treatment, several times before a favorable treatment window is indicated, or upon administration of the analyte. The monitoring can also be done after steps are taken to influence or induce the targeted region to be more receptive to drug uptake (such as by directing external radiation or temperature therapies at the target site).

It is noted that relative or absolute values of the detected signal can be used to assess the intensity or quantify the amount of fluorescence at the site (such as by taking a measurement before the labeled analyte is introduced to have a baseline indication to cancel out background information or by using the ratio of two measurements).

FIG. 13D illustrates two graphs corresponding to different response profiles that can be obtained of the target region using different excitation signals. The top graph illustrates that a first excitation signal can be output at a first intensity (power) level that produces a different response profile compared to the corresponding second graph obtained using a second excitation signal at a different intensity (power) level. The different excitation signals may produce a variation of fluor-intensity over time as shown. For example, the system and/or sensor(s) can be configured to successively output a plurality of different excitation signals, each at a controlled (different) variation of power intensity (such as a first signal at 5 mW and a second at 15 mW). The response to the different emitted excitation light signals can be detected so as to be able to generate optical profiling data about the target region, such as a tumor or other target site. In addition or alternatively, different excitation wavelengths can be used. Thus, a plurality of different excitation signals at a different selected intensity, power and/or wavelength can be generated and the response wavelengths and/or intensity detected by the sensor and relayed to the external reader or processor. The controlled variation can be a stepwise (incremented, decremented or combinations of same) variation. The different excitation signals may be generated by the same excitation source or different sources held within the sensor body.

In particular embodiments, a subject can be undergoing treatment for a cancerous tumor. A quantity of a fluorescent analyte, for example, a fluor-labeled analyte (alone or combined with other ingredients or substances), can be administered to the subject. The quantity or concentration of the substance or analyte may be such that it acts as a pre-therapeutic treatment test dose, rather than a therapeutic dose, which is delivered in advance of the therapeutic dose to assess or predict the clinical efficacy of a treatment prior to delivery of the treatment itself. The labeled analyte or substance can be delivered either systemically, locally, or both.

In certain embodiments, a small test or sub-therapeutic dose of a labeled substance or analyte such as a fluor-analog of a chemotherapy drug, pharmaceutical or Ab can be administered to the subject proximate in time (and/or before) a treatment session (for which a non-labeled version of the pharmaceutical can be used to therapeutically treat the cancer). As used herein, a "small" dose means a dose that is less than a therapeutic dose. The detected fluorescence can provide kinetic or predictive information about the likelihood of the success of the treatment and allow a potential clinician to proceed with the planned treatment, delay the treatment, exclude one or more of a treatment, or select a different pharmaceutical agent for treatment. In certain embodiments, the labeled dose can be sized in an amount that is between about a 0.1%-60%, and can be about 1-10% of that of a corresponding therapeutic dose. The dose may be sized according to weight (children may receive doses in the lower portion of the range with large adults receiving doses at or above the typical range).

Figure 13F:
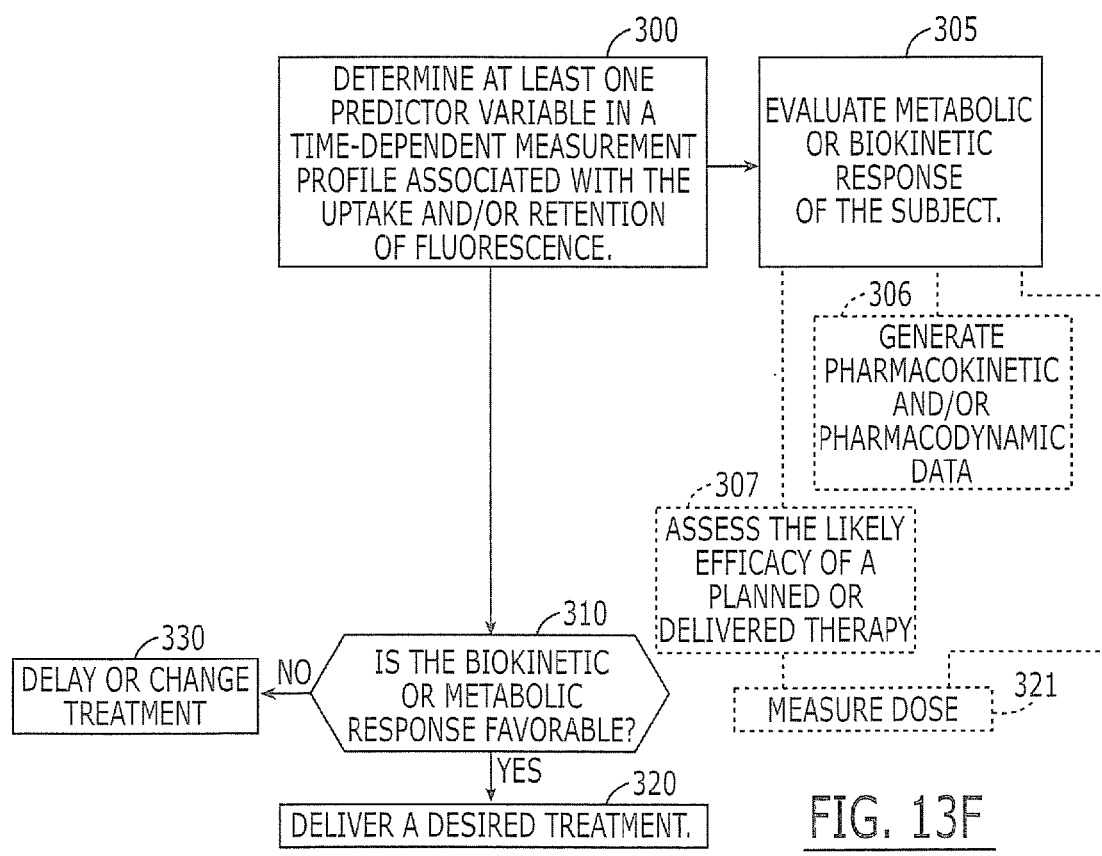
FIG. 13F is a block diagram of operations that may be carried out according to embodiments of the present invention.

FIG. 13F is a block diagram of operations that can be carried out according to embodiments of the present invention (the operations may be directed or carried out by a computer program). The operations obtain and use at least one predictor variable taken from a time-dependent measurement profile associated with the uptake and/or retention of fluorescence in the tissue. The term "predictor variable" means a predetermined parameter associated with fluorescence intensity that is predictive of an internal activity or response of interest that can be used to calculate internal dosage or internal action or reaction. The predictor variable can be a plurality of calculated kinetic factors. The kinetic factors can be used to determine whether a biokinetic response (which can mean changes in the biological or physiological function of the subject) is favorable in order to make therapeutic treatment decisions according to embodiments of the present invention. As shown, at least one predictor variable (which can be a plurality of predictive kinetic factors) associated with the uptake and/or retention of fluorescence is determined (block 300). The predictive variable can include those associated with the response profiles as described above with respect to FIGS. 13A-E. The method then assesses the metabolic activity of the subject (block 305) and/or whether the biokinetic response of the subject is favorable (block 310). If so, in certain embodiments then a desired treatment can be delivered to the subject (block 320). If not, then a treatment can be delayed or postponed or altered (block 330) to attempt to increase the chances for a favorable therapeutic response. The method may also consider the available therapy types and select one which is more likely to achieve a clinically satisfactory outcome based on tumor type, certain kinetic or activity based predictive factors, or other patient information (such as age, treatment number (such as whether it is a primary or secondary or tertiary treatment)) or the like. Alternatively, or additionally, the metabolic evaluation (block 305) can be used to study or evaluate pharmacokinetic data (block 306) and/or to assess the efficacy of a planned or delivered therapy (block 307). The predictor variable(s) can be used to measure the received dose (block 321).

Figure 14:
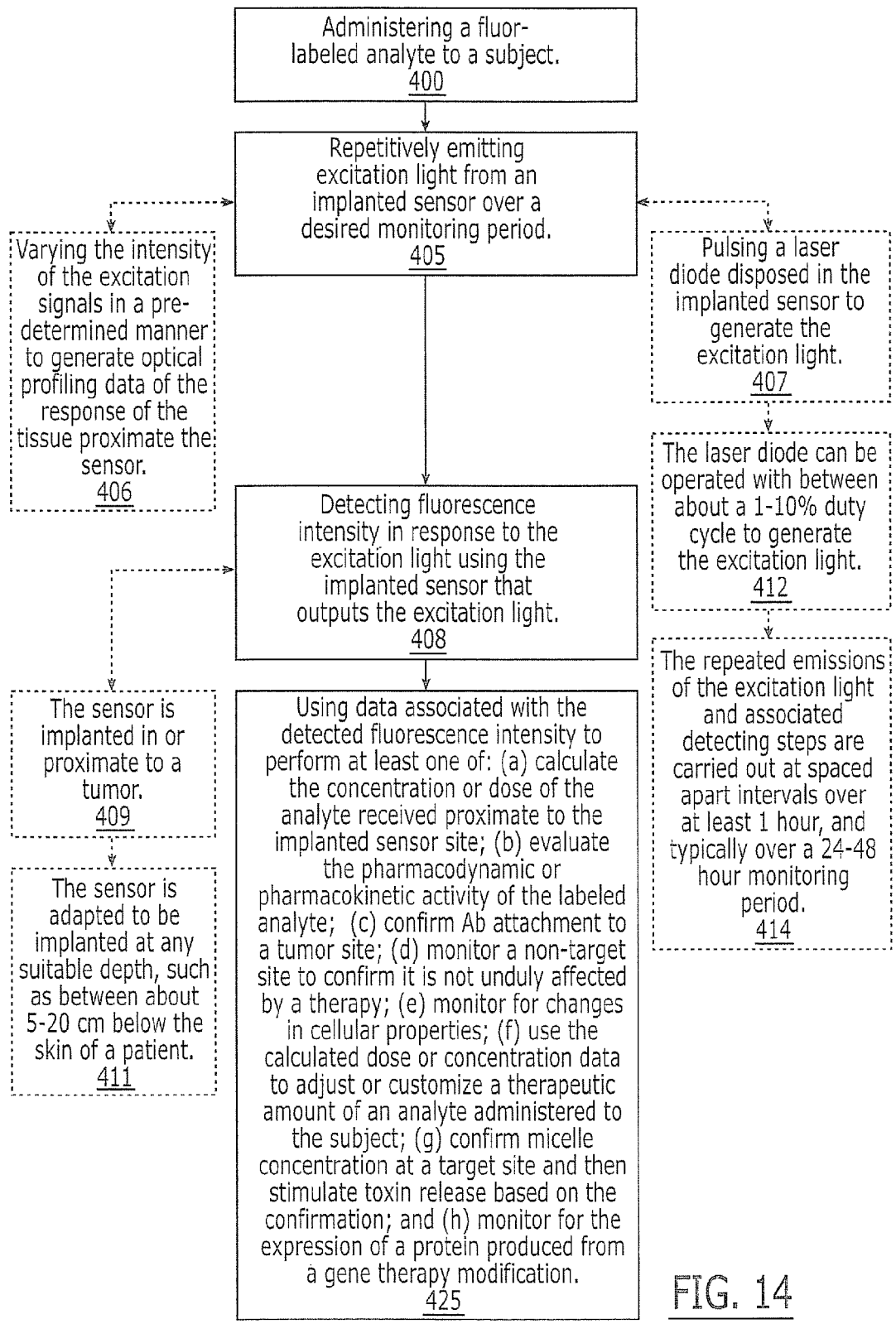
FIG. 14 is a block diagram of operations that can be carried out according to embodiments of the present invention.

FIG. 14 illustrates operations that can be carried out according to embodiments of the present invention. As shown, a fluor-labeled analyte can be delivered to a subject (block 400). Excitation light can be emitted from an implanted sensor over a desired monitoring period (block 405). Fluorescence intensity can be detected in response to the excitation light using the implanted sensor that outputs the excitation light (block 408). Data from the detected fluorescence intensity can then be used to perform at least one of: (a) calculate the concentration or dose of the analyte received proximate to the implanted sensor site; (b) evaluate the pharmacodynamic or pharmacokinetic activity of the labeled analyte; (c) confirm Ab attachment to a tumor site; (d) monitor a non-target site to confirm it is not unduly affected by a therapy; (e) monitor for changes in cellular properties; (f) use the calculated dose or concentration data to adjust or customize a therapeutic amount of an analyte administered to the subject; (g) confirm micelle concentration at a target site and then stimulate toxin release based on the confirmation; and (h) monitor for the expression of a protein produced from a gene therapy modification (block 425).

In certain embodiments, a laser diode disposed in the implanted sensor can be pulsed to generate the excitation light (block 407). The laser diode can be operated with between about a 1-10% duty cycle to generate the excitation light (block 412). The repeated emissions of the excitation light and associated detecting steps can carried out at spaced apart intervals over at least about 1 hour, and typically over a 24-48 hour monitoring period (block 414).

In certain embodiments, the intensity of the excitation signals can be varied in a predetermined manner to generate optical profiling data of the response of the tissue proximate the sensor (block 406). In particular embodiments, the sensor is implanted in or proximate to a tumor (block 409). The sensor is adapted to be implanted at any suitable depth, such as up to about 25 cm, and may be between about 5-25 cm, and may typically be between about 10-20 cm, below the skin of a patient (block 411). It will be understood that the depths provided herein are provided for exemplary purposes only and that embodiments of the present invention should not be limited to this configuration. For example, the sensor may be implanted at depths from about 1 cm to about 25 cm without departing from the scope of the present invention.

As previously discussed, the sensor may also be configured as a minimally invasive catheter based-probe (inserted into a natural body lumen). In other embodiments, the sensor probe can use an invasive fiber optic probe that is configured to be implanted with the tip portion disposed at the site of interest. The probe tip can be implanted by making a small incision with a scalpel and inserted at the target site with a large gauge needle. The fiber optic probes may employ one or more fibers sized from between about 250 microns to 1 mm. In these embodiments, the light source and multi-channel analyzer can be externally (out of the body) placed. The sensor can be placed to within about 1 mm or less (or to the resolution of the guiding device) from the site of interest, particularly if CT (Computed Tomography), ultrasound guidance, Magnetic Resonance Imaging (MRI) and/or X-ray is used. It is also possible to place the tip of the sensor probe at a tumor periphery and observe data from within a few millimeters of the tumor periphery.

It will be understood that although embodiments of the present invention including fiber optic probes are discussed herein as having at least tips implanted in vivo, embodiments of the present invention are not limited to this configuration. For example, fiber optic probes may be used ex vivo or in vitro according to some embodiments of the present invention.

In some embodiments according to the present invention, referring to FIG. 1A, a fully implantable telemetrically operated sensor 10 can be used to excite and detect fluorescence in vivo. The excitation source can be a laser diode and a photodiode can be used for detection. Thin film dielectric layers can be applied to the outer wall surfaces (Chroma: Brattleboro, Vt.) of these devices to create selective bandpass filters. The photodiode can be used to integrate substantially all wavelengths in the emission spectrum to increase the signal-to-noise ratio. These components and their corresponding circuitry can be placed in a miniaturized biocompatible elongate capsule 10c similar to that of a radiation sensor described in U.S. Pat. No. 6,402,689. The biocompatible capsule 10c may have a diameter of between about 2-3 mm and a length of less than about 20 mm.

The sensors 10 can be surgically implanted in an area of interest and telemetrically operated. Testing has been done on the radiation sensor's glass capsule (having a corresponding size and shape contemplated for certain embodiments of the fluorescence sensor) in which 12 rats were implanted with either Parylene C coated or uncoated glass capsules. After 90-122 days, a fibrous encapsulation of 10-100 microns was observed in all animals. No inflammatory reaction due to the implant was evident, nor was significant migration from the implant site. Furthermore, human trials have showed no significant migration of the implantable sensors 10.

Figure 1B:
FIG. 1B illustrates implantable sensors having anti-rotation features according to embodiments of the present invention.

As illustrated in FIG. 1B, sensors 10 according to some embodiments of the present invention may include anti-rotation features 15 to anchor and/or inhibit the sensor rotation or migration inside the patient. For example, examples of anti-rotation devices are discussed in commonly assigned U.S. patent application Ser. No. 10/353,857, entitled Implantable Sensor Housing, Sensor Unit and Methods for Forming and Using the Same, filed Jan. 18, 2003, the disclosure of which is incorporated herein as if set forth in its entirety. Accordingly, details of the anti-rotation features 15 will not be discussed further herein.

In operation, light at a selected wavelength(s) is transmitted at a first intensity level to illuminate tissue, membrane, or cells located proximate the sensor 10 or sensors 10 in the body. Subsequently, the fluorescently emitted light is detected by the detector held inside the sensor capsule 10c. The fluorescently emitted light will have a longer wavelength and less energy than that of the excitation light.

For systems where multiple sensors 10 are used, the external reader or processor can be configured to serially poll each sensor at the same frequency with each sensor having a unique RF identification data bit or bits allowing identification and individual interrogation. The multiple sensors may be placed adjacent or in tumors or proximate normal or non-targeted tissue or organs. Such placement can be selected to allow for external monitoring of doses received proximate sensitive and/or non-targeted sites, such as the thyroid, heart, or proximate the tumor or targeted treatment region.

The implantable sensor unit 10 shown in FIG. 1A includes electronics 10e and antenna or coil 10a configured to allow wireless communication to the external reader 30. The sensor unit 10 can also be configured to sense radiation and, as such, may also include a RADFET that operates with a threshold voltage "Vth" shift that is proportional to absorbed radiation dose. In certain embodiments, at least one, and typically a plurality of the implanted sensor units 10 can be configured to monitor fluorescence, radiation dose and temperature. As such, the sensor 10 can include a RADFET, an optical detector and light source, and a digital temperature sensor. The temperature data and radiation dose data can be used to help administer hyperthermia/radiation combination therapies.

The sensor unit 10 can be inductively powered via an inductively coupled internal coil 10a. The sensor unit 10 can be held in a hermetically sealed encapsulated housing, such as a glass capsule or other medically suitable material that is substantially impermeable. The sensor unit 10 electronics 10e can include a micro- (or nano-) processor controller that controls data acquisition and reader/sensor unit communications that can be mounted on a ceramic substrate. The electronics 10e can include custom chip designs with routings to semiconductor chips provided for data acquisition. The sensor unit 10 can include a bidirectional antenna. The sensor unit 10 can be configured with digital communication components (such as a digital signal processor) using a 12-16 bit data acquisition that can provide about a 1 mV or less resolution (or better) of the Vth measurement and may operate with a 16-bit CRC error checking capacity. The electronics 10e can be potted in Class VI USP epoxy and hermetically sealed inside the capsule 10c. The external surface or body of the capsule can be coated with a Parylene C material or other biocompatible coating configured so that the fluorescence excitation and response light is transmittable through the sensor wall. The sensor unit can be EO sterilized and adapted to be suitable for chronic in vivo implantation as described. The sensor body or portions thereof, may be radio-opaque for visual contrast in CT scans and port films and the like. Additional description of exemplary sensor unit housing configurations can be found in co-pending U.S. patent application Ser. No. 10/353,857.

In certain embodiments, the system 10 can be configured to individually selectively (serially) poll, address, and/or interrogate a selected implanted sensor unit 75. The sensor units 75 can be configured to operate or communicate with the reader at the same frequency. To control and/or identify which sensor unit 10 is in active communication mode, a single or multi-bit identifier can be generated and used in the data stream.

Figure 2:
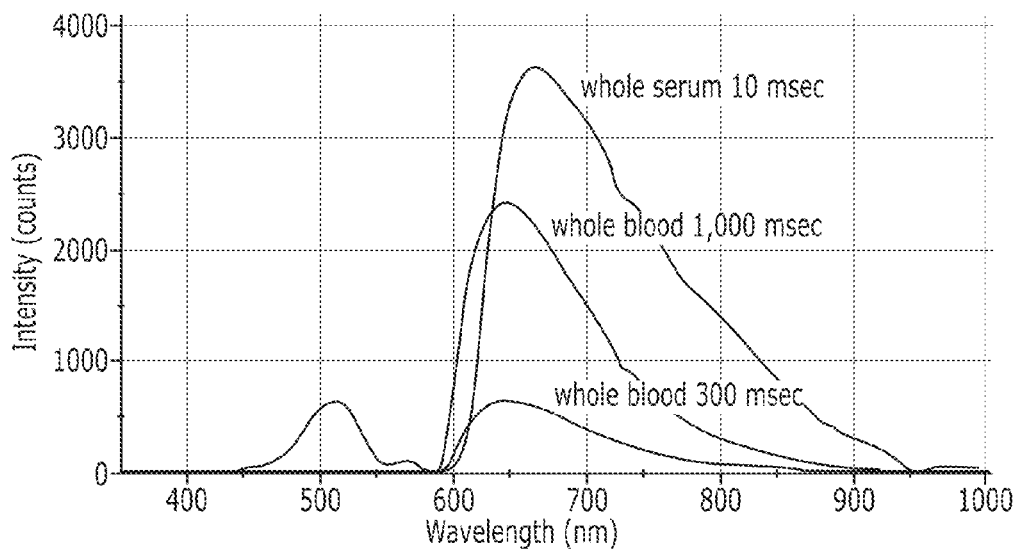
FIG. 2 is a graph of intensity versus wavelength of the transmittance of light through dog blood and serum using the integration time of a multi-channel receiver.

In certain embodiments, the fluorescence sensor or probe 10 will be configured to project excitation light through localized tissue so that the light penetrates through layers of fascia that may be encapsulating the sensor 10. Testing has shown that a laser diode can produce light that penetrates approximately 20 mm through tissue with some trade-off in intensity due to tissue attenuation. Testing on nude mice has also shown that the catheter-based fluor-sensor and excitation light source can also be used to generate excitation light that penetrates to a depth of many millimeters. Thus, biofouling associated with chronic implantation of the sensor 10 should not inhibit operation of the device with respect to signal intensity since the laser light will penetrate layers of adsorbed proteins and lipids and will transmit sufficiently through muscle, blood, serum, etc. FIG. 2 shows the transmittance of lasers (intensity counts) at various wavelengths through dog blood and serum using various integration times (10 ms, 1,000 ms, and 300 ms) of a multi-channel analyzer.

In operation, the fluorescence monitoring system can quantify relative fluorescence by summing the number of counts per wavelength over a set or predetermined integration time cycle. After each time cycle, a new spectrum of intensity vs. wavelength, such shown in FIG. 2, is produced. In operation, intensity increases as more fluor (fluorescence emission) passes in front of the detecting diode and/or fiber optic element. The maximum values of the spectra themselves or the integrated values can be compared in tumor vs. normal tissue.

In certain embodiments, during evaluation, a baseline signal can be obtained in any tissue of interest before and after the fluorescent analyte is administered. In embodiments of the present invention using a fluor-labeled analyte, the labeled analyte such as antibodies are administered so the pharmacokinetics and pharmacodynamics of the uptake can be monitored and recorded in real time as the fluor and antibody distribute throughout the body. Experiments have shown that there is a preferential uptake in tumor for the appropriate antibody, and that fluor alone does not have the same distribution patterns as fluor conjugated to antibody. Calibration can consider both in vitro assay and in vivo comparison with plasma or other selected biomaterial values.

Figure 3:
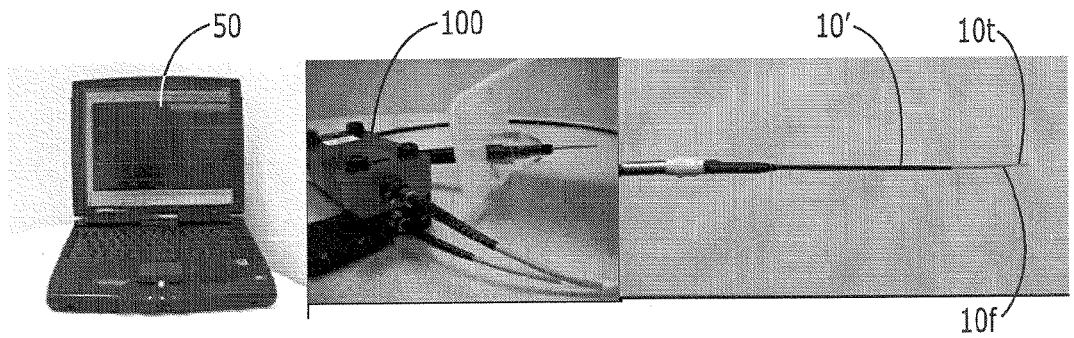
FIG. 3 is a screen print out of components of a fiber optic fluorescence probe system according to embodiments of the present invention.

C-14 labeling is a useful tool for studying the kinetics of organic compounds, even ones with very small molecular weights like glucose (180 Daltons). See commonly assigned U.S. patent application Ser. No. 10/127,207, the contents of which are hereby incorporated by reference as if recited in full herein. However, fluorescent markers have advantages in other situations, e.g., Ab labeling or gene expression. Radiolabel and fluorescent label sensors provide a powerful tandem for a wide range of studies in vivo. Initial experiments with the catheter-based version of the fiber-optic fluorescence probe 10' (FIG. 3) have been completed. The catheter-based probe 10' is shown in FIG. 3 and has a computer interface 50, a fiber optic probe 10f with a tip 10t that is configured for in vivo bioplacement, a diode illumination source, and an optical multichannel analyzer 100, such as that available from Ocean Optics (Dunedin, Fla.). As will be discussed further below, testing was performed to determine the resolution of the probe; these measurements were conducted with ALEXA FLUOR 594 (Molecular Probes: Eugene, Oreg.). Calibration runs with the probe in gelatin with 3% milk (to scatter light) showed sensitivities in the ng/ml range, more than adequate for assays with therapeutic compounds.

As described above, in certain embodiments, a fully implantable diode laser/photodiode pair can be configured to excite and readout fluorescent labels, such as dyes. The implantable fluor sensor can give information at clinically acceptable subsurface depths and/or on a chronic basis. However a fiber-optic based probe, such as that shown in FIG. 3, is robust, convenient, and may be attractive for some clinical applications for more superficial tumors or ex vivo or in vitro analysis. Light emitting diodes (LED's), laser diodes, and photodiodes have been developed for many applications. Sensors using laser diodes can be configured similar to sensors using LED's, except that, in the former, an integral optical cavity is created (known as a Fabry Perot cavity) that narrows the light bandwidth considerably and increases the light output. In certain embodiments, the face of the laser diode used in the implantable version can be coated with a dielectric filter to create an optical bandpass that substantially matches the excitation wavelength of the appropriate fluor. Light coming out at angles beyond about 30° with respect to normal incidence may be too far out of band and thus a physical collimator can be used to limit the angular dispersion. The photodiode can be filtered and collimated in the same way (where the filter is deposited such that the emission spectrum of 594 or 647, or other selected wavelength depending on the fluor used, is allowed to pass).

In order to conserve power, in certain embodiments, the laser diodes can be operated in a pulsed mode. The basic phenomenon of fluorescence occurs on the femtosecond to nanosecond timescale. Pulse durations in the millisecond range are considered to be adequate for excitation of fluor-labeled analytes in the target tissue to desired depths using excitation light from a light source having a power in the milliwatt range. The duty cycle can be selected to allow the total power sent by telemetry to the implant to be to reasonable levels while at the same time the laser diode can supply light output in the milliwatt range.

Figure 6:
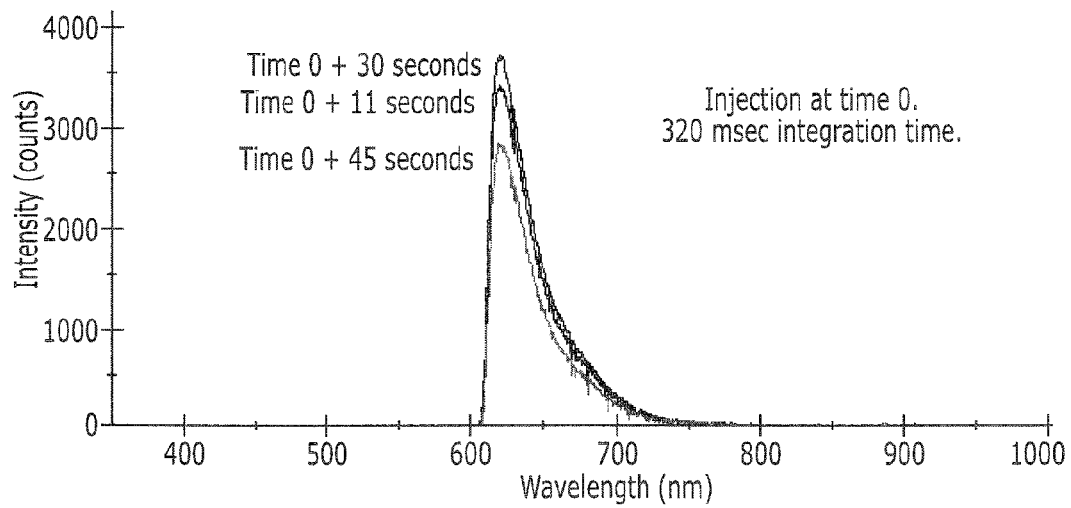
FIG. 6 is a graph of intensity versus wavelength of ALEXA FLUOR 594 hydrazide (Molecular Probes, Inc., Eugene, Oreg.) in a Fisher 344 Rat at three different points in time from administration in the rat tail vein (t=0).
Figure 7:
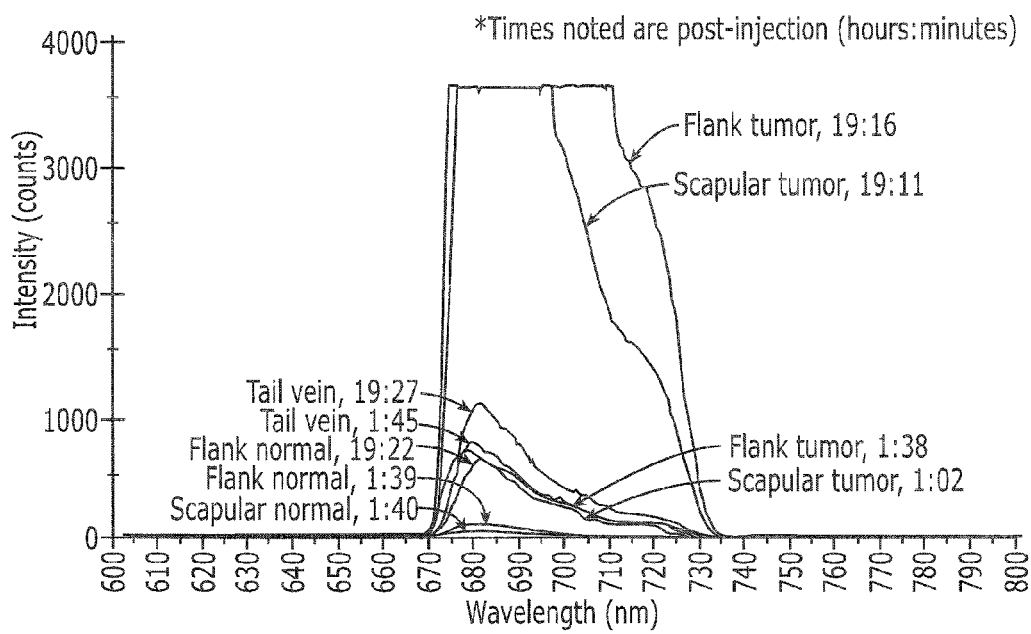
FIG. 7 is a graph of intensity (counts versus wavelength) at various post-injection times, after injection of labeled HERCEPTIN, illustrating uptake and retention in nude mouse with human BT474 scapular and flank tumors.
Figure 8:
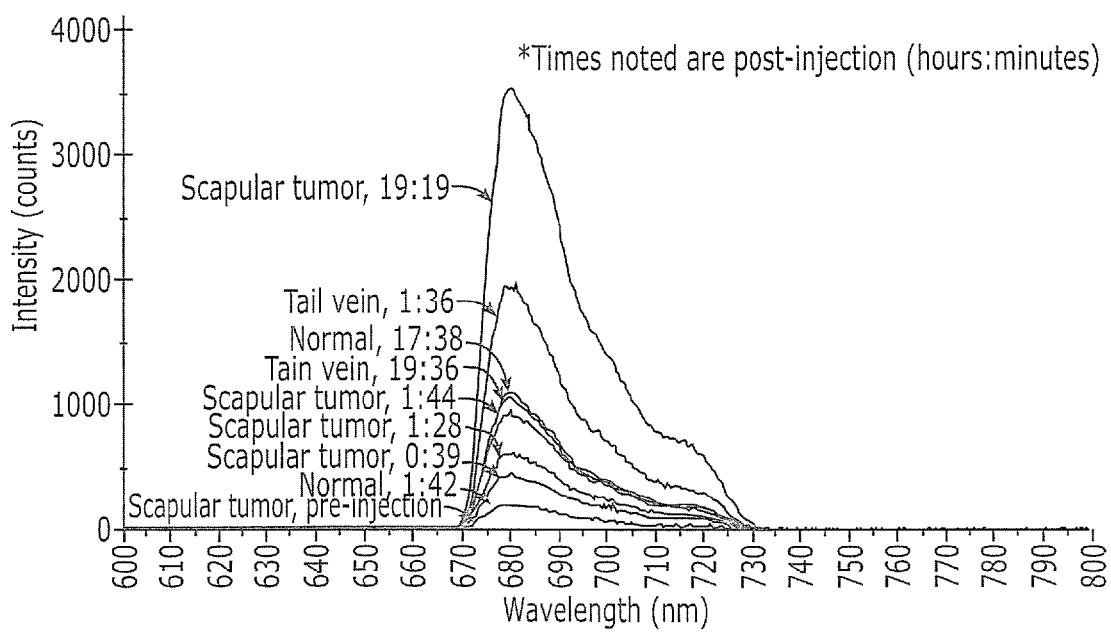
FIG. 8 is a graph of intensity (counts versus wavelength) at various times, including a plurality taken after injection of labeled ANTI-CD20, illustrating uptake and retention in nude mouse with Raji Burkitt's human lymphoma tumor.

Unlike the emission spectra shown in FIGS. 6-8 created by the fiber-optic probe and multi-channel analyzer, the photodiode can integrate the light allowed through its optical bandpass filter. This is desirable for certain applications because there may be no frequency shift information of relevance. In operation, in certain embodiments, some fluors can show a frequency shift with pH or oxygen tension. As these are parameters of potential interest in oncology, a modified sensor configuration could be built where two photodiodes, with non-overlapping bandpass filters, are used in a ratiometric way to determine spectral shift. In certain embodiments, the implantable sensor 10 can employ a pair of laser diode/photodiodes side-by-side in the body of the tube shown in FIG. 1. In some embodiments, the size of the tube may be even smaller, such as between about 2.0-2.2 mm in diameter.

Some embodiments of suitable sensors seas with an air interface between the diodes and the tube wall. In further embodiments, the interior of the capsule can be filled with a compound matching the refractive index of the capsule's glass wall. The latter version can form a hemi-cylindrical lens between the diodes, and the sample outside the tube (there will be some lensing with the air version as well, but may be less pronounced). The illumination patterns can be documented in vitro and the relative merits of the illumination fields assessed.

Figures 9A, 9B:
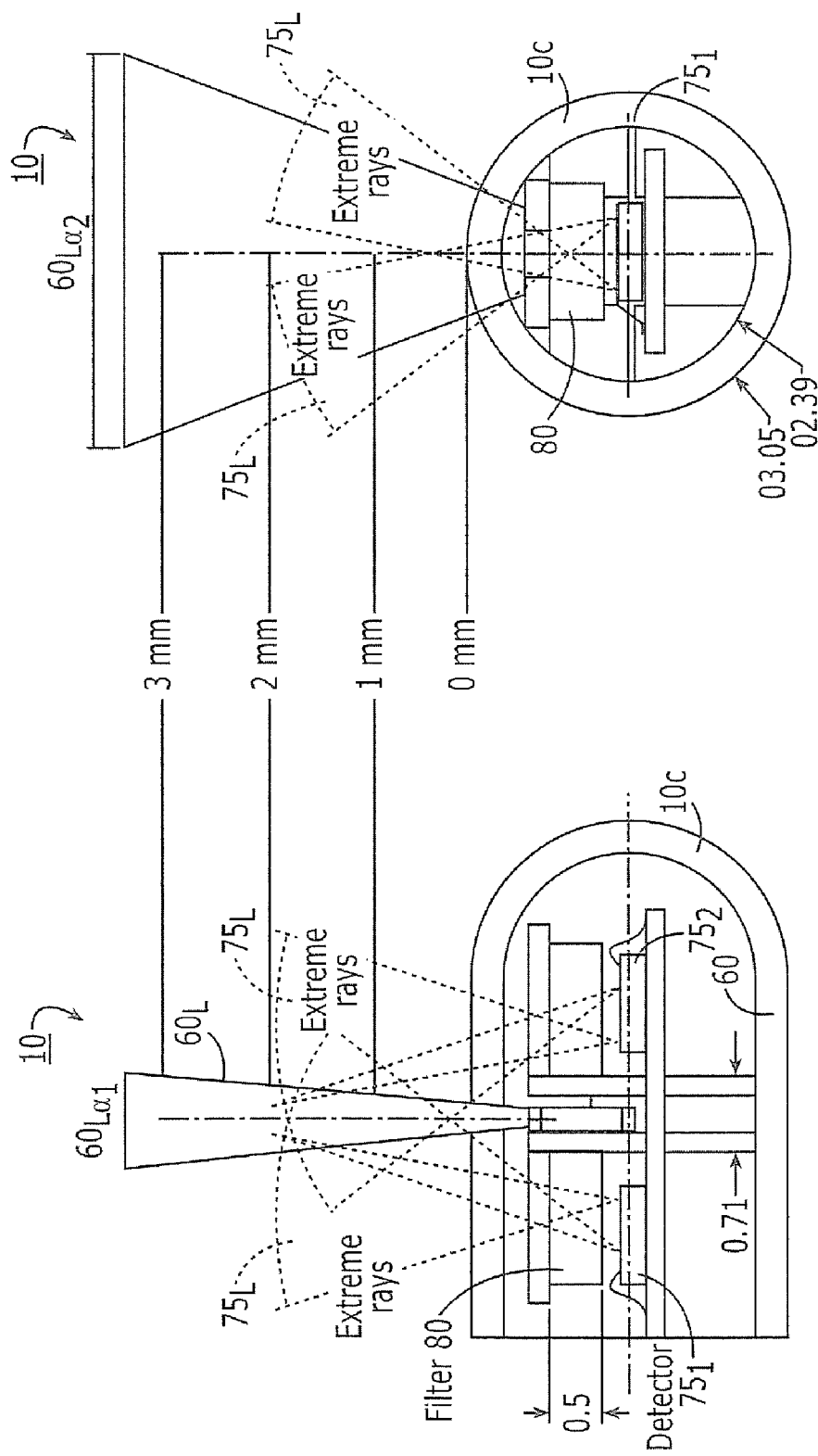
FIG. 9A is a side view of a diode-based implantable sensor according to embodiments of the present invention.
FIG. 9B is a cutaway end view of the device shown in FIG. 9A.

FIGS. 9A and 9B show a cross section of one implantable fluor-sensor 10 configuration using two side-by-side aligned detectors $75_1$, $75_2$, and laser diode 60 excitation source inside the capsule body 10c of the sensor 10. As shown, the laser diode 60 transmits light $60_L$. The excitation light $60_L$ may have two different light dispersion angles $\alpha_1$ of about 10° and $\alpha_2$ of about 40°. This intrinsic dispersion is the first determiner of field of view. Lensing action can be used to adjust the light cone to some degree (the embodiment shown in FIG. 9A does not assume focusing). The sensor 10 can be configured to measure and increase or optimize the effective field-of-view. Relative spectra can be recorded to follow the kinetics of binding. In some cases, a baseline reading can be taken prior to injection of the fluor. In order to accurately normalize the photodiode detector 75 output for concentration in vivo, the attenuation of the target tissue may be taken into account. One way to normalize the fluorescence data is to take a baseline absorption reading with an unfiltered photodiode and compare that signal to a known tissue test value. This reading can be implemented by adding a second photodiode without the bandpass filter 80 shown in FIGS. 9A and 9B. This configuration does not require a cylindrical filter (as will be described further below).

In certain embodiments, as shown in FIGS. 9A and 9B, a first detector $75_1$ can be configured without the filter (although shown with filter 80) so as to be able to detect laser light that reenters the sensor while the second detector $75_2$ is filtered and detects the fluor-emission light. The light detected by the first detector $75_1$ can be monitored and its intensity can provide information about the attenuation of the laser signal and/or about the ability of the laser light to penetrate tissue. For example, for dense or non-transmissive tissue, the detected laser light may be more intense than where the laser light is substantially free to emit and travel a depth into proximate tissue away from the sensor. This non-filtered data can be used to adjust or normalize the detected fluor-signal data from detector $75_2$. If less laser light is transmitted, less fluor-light may be expected. Further calibration of the fluorescence probe can be carried out by comparing the intensity of the signal of known concentrations of fluor obtained in vitro, with intensities observed in vivo.

The sensors described herein can be configured to be relatively immune to biofouling issues that occur with galvanometric sensors placed in vivo. Studies of an implantable radiation dosimeter as described above, have shown that glass capsules elicit a minimal foreign body response, typically, even when chronically implanted for weeks or months, leading to encapsulation by fibroblasts to a thickness of between about 50-100 µm. The excitation light and emitted fluorescence can easily pass through this layer. The fluor sensors 10, 10' of the present invention can probe activity at subsurface locations in tissue several millimeters (typically up to about 20 mm) away, and may also pass through any thin layer of fascia as described above.

In some embodiments according to the present invention, a fluor from an exogenous source can be used. In such cases, the fluor signal can be used to quantify the amount of labeled analyte in the tissue or it can monitor for the activation or extinction of the fluor signal due to some cellular or natural process. The value of this signaling capability is that it may identify events like antigen expression changing, apoptosis setting in and the like. Some embodiments, according to the present invention, may also include a matrix for release of a fluor-labeled antibody held on the sensor body, but the sensor may be configured without such a matrix and be configured to project excitation light and detect the illuminated fluorescence in response thereto based on the presence of a fluor-labeled analyte such as a labeled antibody that are externally administered.

In some embodiments according to the present invention, the quantification information can be used to titrate the amount of a therapeutic agent given during therapy. For an Ab therapy, the dose may be adjusted based on how effectively a first administration gets to the tumor target. Techniques can also be used to release toxins from micelles that also can contain fluor. So, for example, the above implantable device 10 can be used to determine proper micelle concentration at the target. The data can be used to direct or stimulate the release of the toxins.

In some embodiments according to the present invention, the concentration of labeled analyte or compound can be quantified as a function of time of using the implantable sensor. In some embodiments according to the present invention, index-matched epoxy can be used to couple the laser diode and photodiode to the glass (or other biocompatible and optically suitable material) enclosing the electronics of the sensor so that internal reflections are inhibited. In some embodiments according to the present invention, the intensity of the emitted light can be varied in a stepwise, incremental or decremented fashion to generate optical profiling information about the tumor. As noted above, the laser diode 60 can be pulsed. The pulse excitation can be used, for example, to quench fluorescence and watch for recovery. In other embodiments, the pulsation can be carried out to avoid quenching the fluorescence to maintain the signal over time. In some embodiments according to the present invention, a dense (in time) sampling of fluor concentration can be generated over longer cycle times (hours). This approach may use the implanted sensor confirmation and/or the fiber probe based techniques.

In particular embodiments, one range of excitation (diode laser) wavelengths can be between about 630-660 nm (nanometers) for a fluor such as ALEXA FLUOR 647 that is excited at 647 nm and emits fluorescence light at about 665-695 nm. The optical power can be in the 1-20 mW range. The duty cycle will vary depending on whether the laser bleaches the fluor or not. In some tissues, 10 mW can destroy the signal away in a couple pulses. Thus, a duty cycle in the 1-10% range is expected. Also, at the higher power range, the laser could burn out if run at 100%. Finally, if the sensor is implanted relatively deep in the body, there may be insufficient power to couple enough to run the sensor electronics at 100%. In particular embodiments, the operating frequency will be in the 10-1 KHz range.

It will be understood that any particular wavelengths discussed herein are provided for exemplary purposes only and that embodiments of the present invention are not limited by these examples. For example, the wavelength ranges discussed above may be from about 400 to about 900 nm without departing from the scope of the present invention.

Stated differently, in certain embodiments, the laser diode 60 is pulsed at a frequency of 10-1000 times per second. When it is in the "on" half of the cycle, the on time can be reduced to between about 1-10% of the possible amount of time. For example, the laser can be pulsed at 10 Hz, with 10 firings in a second and, at a 10% duty cycle, it would be on for about 0.01 seconds per shot.

In particular embodiments, the detector 75 can be operated so that the signal (count) is integrated over about 1-120 seconds in total, depending on the concentration. The measurement can be repeated every so many minutes for a desired monitoring interval, such as between about 24-48 hours.

Figure 11A:
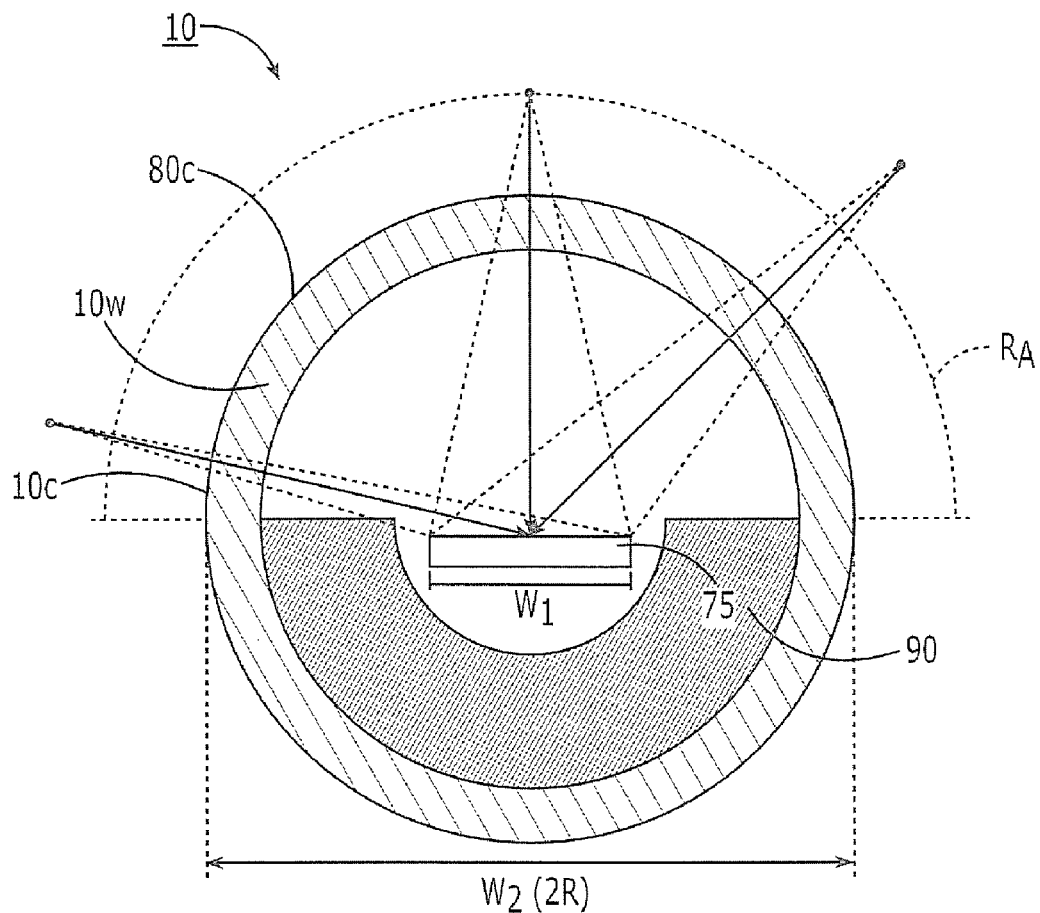
FIG. 11A is a schematic illustration of a section (end) view of a sensor having a partial-cylindrical filter according to embodiments of the present invention.
Figure 11B:
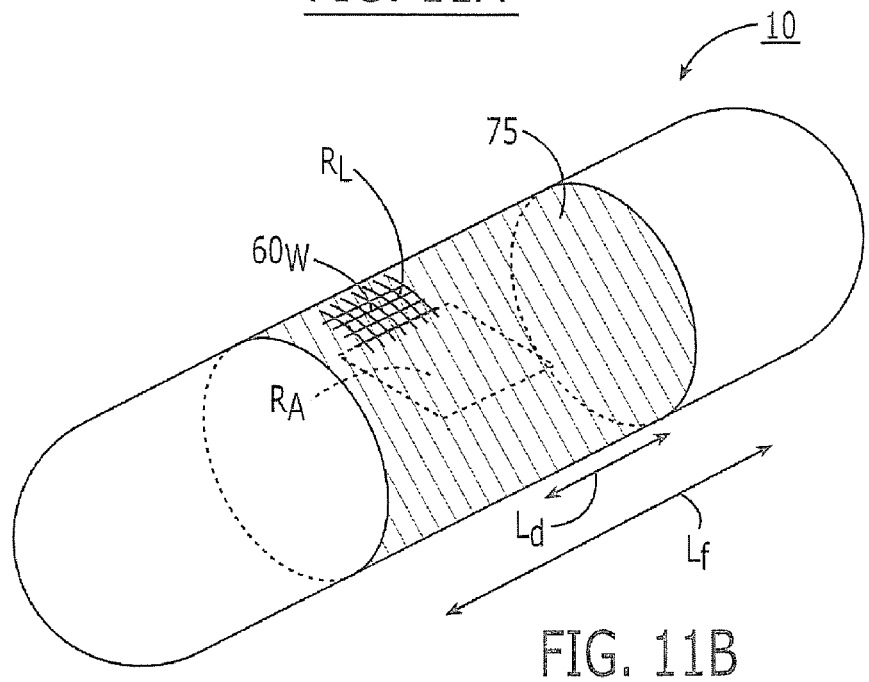
FIG. 11B is a perspective view of the sensor shown in FIG. 11A illustrating a semi-cylindrical filter and a compound filter forming an optic window to selectively allow laser output according to embodiments of the present invention.
Figure 11C:
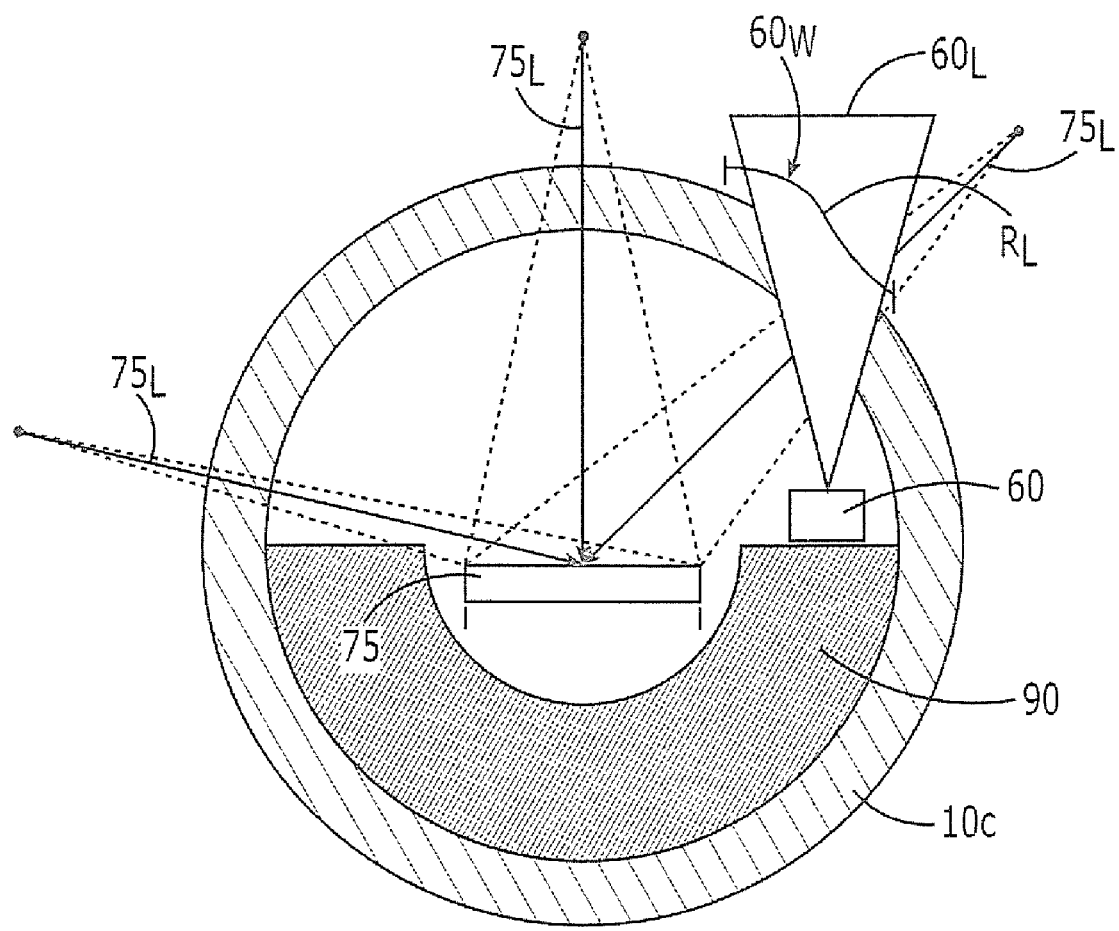
FIG. 11C is a schematic illustration of the sensor shown in FIG. 11A using placement of the laser to allow the laser light out by impinging on the cylindrical sensor wall at an angle greater than a critical angle according to embodiments of the present invention.

In some embodiments according to the present invention, a cylindrical absorption filter 80c can be provided with a filter that in operation, it covers at least about 180 degrees of the wall of the sensor capsule 10c so as to gather increased incoming fluorescence signal at the photodetector 75 as shown for example in FIGS. 11A-11C. As shown, the filter 80c may be generally cylindrical and continuous over the perimeter (360 degrees) of the housing body of the sensor 10c for a desired length. Alternatively, the filter 80c may be formed as a generally semi-cylindrical filter (FIG. 11B) covering only a portion of the perimeter (such as the 180 degrees above the detector), particularly if only one detector 75 is employed. Thus, as used herein, the term "cylindrical" filter includes generally semi-cylindrical filter configurations.

Dielectric filters are angle-dependent. Conventionally, unless the incoming light is within about 15-30 degrees of normal incidence, the filter may not work properly. Thus angular limitation, in turn, can limit the light gathering power of the sensor device. As shown in FIG. 11A, a partially cylindrically shaped filter 80c is configured to cover or overlie at least about 180 degrees of the wall of the capsule over a desired length can define an active incoming fluor-light region "$R_A$" that allows for about a 180-degree field of view over a portion of the sensor body 10c. The filter 80c may be formed on the interior surface or exterior surface of the sensor wall 10w. In certain embodiments, a wavelength blocker modifying the absorptance of the wall 10w can be coated or formed over the wall. The coating may be provided by a stack of dielectric anti-reflection layers that are deposited on the outside surface of the cylindrical wall 10w. Other coatings or optical adjustments may be used to provide the desired filter range.

Figure 12:
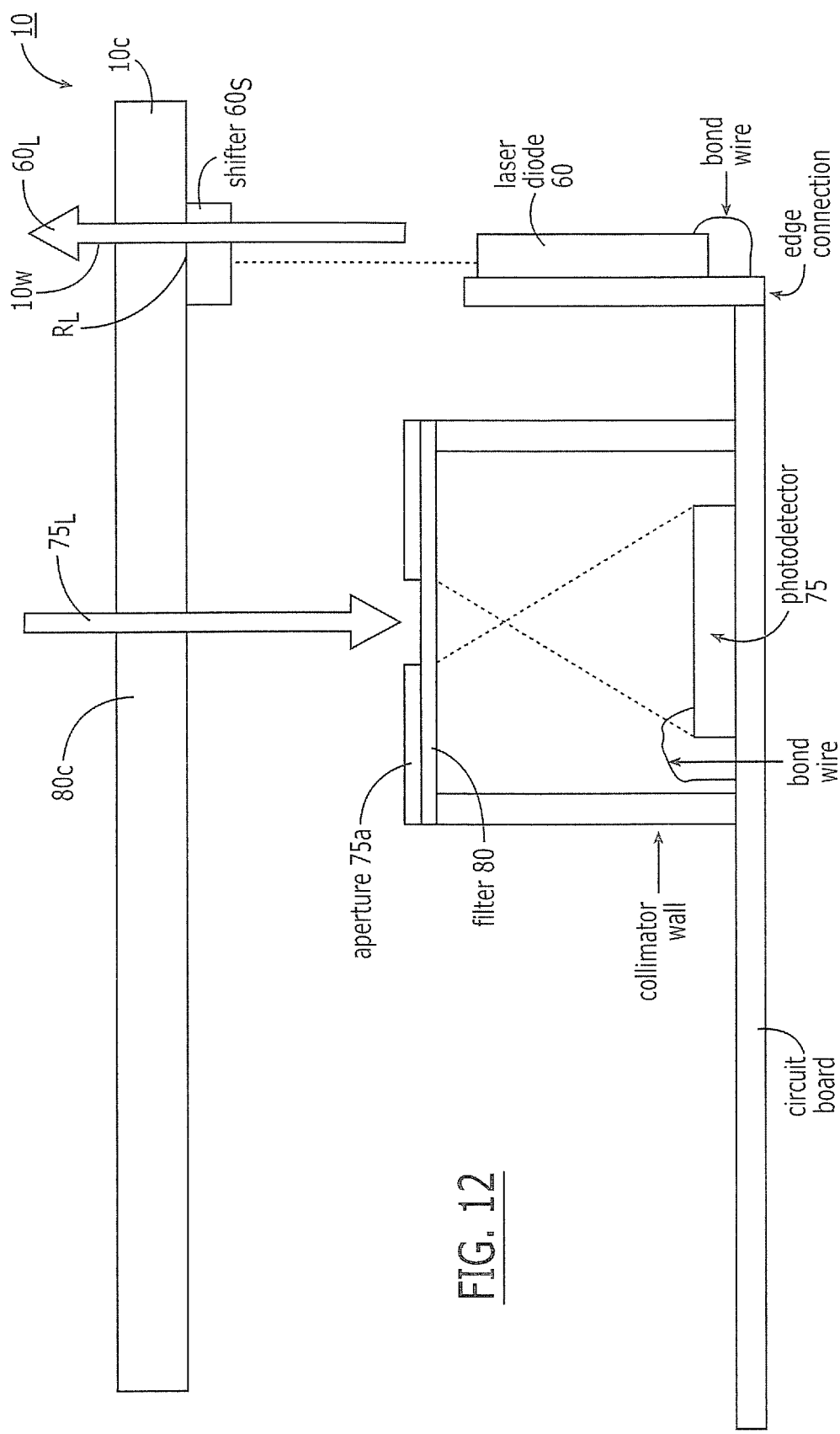
FIG. 12 is a schematic illustration of another embodiment of a sensor detector and excitation configuration with a compound filter according to embodiments of the present invention.

To allow the excitation light to be projected or emitted by the device, an optic window 60w (space or opening in the cylindrical filter 80c) can be formed on the sensor wall. FIGS. 11B and 12 also illustrate the use of a compound filter placed over a selected region $R_L$ of the wall 10w to allow the laser light to pass out of the sensor body through the filter 80c.

In certain embodiments, the window 60w is associated with a second region "$R_L$" that emits light at a first wavelength in contrast to the remainder of the partially cylindrical filter 80c that is configured to allow light at the fluor (longer) wavelength to enter (and inhibits the excitation light from exiting the body of the sensor if projected thereat). This double layer of material configuration can be described as a compound filter and should reduce the likelihood of false readings due to detection of emitted excitation light rather than fluor-based illuminated emissions while increasing the sensitivity of the fluor-sensor. The optic window 60w can be formed as a selective compound filter (with a second coating or layer that adjusts the filter bandpass). Thus, in this embodiment, no aperture box is required and the fluor-signal can be input into the photodetector over a broad range.

FIG. 11C illustrates another technique for allowing the laser light out of the cylindrical filter 80c. In this embodiment, the laser light source is positioned in the sensor so that the light can get out of the sensor by hitting the cylindrical wall at an angle greater than the critical angle (where the cylindrical filter won't block its release). Thus, alignment of the laser source with the wall of the sensor allows the laser light to pass through the cylindrical filter 80c because the light impinges on the cylindrical sensor wall at an angle greater than a critical angle.

The detector 75 can be configured and sized to be substantially smaller (typically less than about 30% of) the width or diameter of the housing or body of the sensor so that the wall 10w defining the filter 80c is spaced apart from the detector 75 a suitable distance. As shown, the detector 75 can be positioned substantially centrally in the sensor body 10c. The configuration and spacing can be selected to inhibit leakage associated with when the probe (excitation) beam leaks back into the sensor and contaminates the detected fluorescence signal at the detector. Thus, the filter properties (bandpass, size, spacing, length, angular coverage, etc), can be chosen so that the probe light is blocked from detection and the longer wavelength emitted (fluorescence) light is passed during operation.

For example, looking at the rays $75_L$ shown in FIG. 11C, the central ray hits the filter wall at an angle of 90 degrees. Other rays from that same point can reach the edges of the detector 75. The detector 75 can be substantially centrally held in the middle of the sensor body as shown in FIG. 11A. The detector 75 can have an associated width "$W_1$" that is less than the cross-sectional width (diameter) "$W_2$" of the sensor body 10c.

The sensor body and hence, filter 80c, can be configured with respect to the detector 75 so that the angle those non-normal rays make with respect to the cylinder wall is not unduly large and a width of the detector and body of the sensor (defining the filter) selected accordingly. The angles desired can vary based on the filter. One way to express a suitable configuration is:

$$W_1 < 2R/\tan(90-T) \quad \text{Equation (1)}$$

where $W_1$=width of detector in section view, R=radius of cylindrical sensor body, T=maximum angle of acceptance of the filter.

Thus, "T" is some angle away from normal incidence beyond which other (non-desired) light can slip through the filter. T is not an exact parameter, since leakage will start to occur and then get worse. As used herein, T represents the angle at which the leakage rapidly deteriorate worse really fast. A typical working range for T is between about 15-30 degrees. So, for 30 degrees, $W_1 < 1.15$ R and for 15 degrees $W_1 < 0.54$ R.

In certain embodiments, the length "$L_d$" (FIG. 11B) of the detector 75 along the axis of the cylinder body 10c can be configured to be less than:

$$R/\tan(90-T) \quad \text{Equation (2)}$$

where R is the radius of the sensor body and T is the critical angle of the filter. So, as before, in particular embodiments, T may range from between about 15-30 degrees. Then, the detector length $L_d$ would be <0.27R for 15 degrees or <0.58R for 30 degrees. The filter 80c will typically have a longer length than that of the underlying detector 75 and may cover the entire perimeter or terminate at an axial distance or that is short of one or more of the end portions of the body of the sensor.

The filter 80c may be cylindrical and cover substantially the entire radial perimeter of the housing albeit typically over a subset of the entire perimeter axial length "L" of the sensor body.

Although shown in FIG. 11B as being substantially centrally located along the length of the sensor body 10c, the filter 80c and underlying detector 75 can be disposed closer to one end of the sensor body 10c (not shown).

In certain embodiments, two excitation sources with two back-to-back detectors 75 can be disposed in the sensor body 10c with the filter 80c being configured to cover about 300 degrees, and more typically about 360 degrees of the perimeter of the cylindrical body over a predetermined length (not shown).

In operation, the partially cylindrical filter 80c can operate to allow fluor-light reaching the photodiode or detector 75 to pass through the filter 80c at an angle near to normal incidence. An inner coating or material can be applied below the photodetector 75 along complementary (shown as lower) 180 degrees of the perimeter of the cylinder body 10c to reduce internal reflection.

With the filter in place 80c, the aperture 75a (shown in FIG. 10) is no longer needed over the detector 75. However, referring to FIG. 12, (a) a small aperture or shifting filter can be used to make the outer filter 80c invisible to the laser wavelength so as inhibit the filter 80c blocking the exit of the laser light. In the case of (b), the wavelength of the laser light itself is not changed (the small shifting filter reduces the filtering effect of the outer filter) and so once the light is emitted from the capsule, the is less likely to reflect back into the capsule, which could create a spurious signal.

Figure 10:
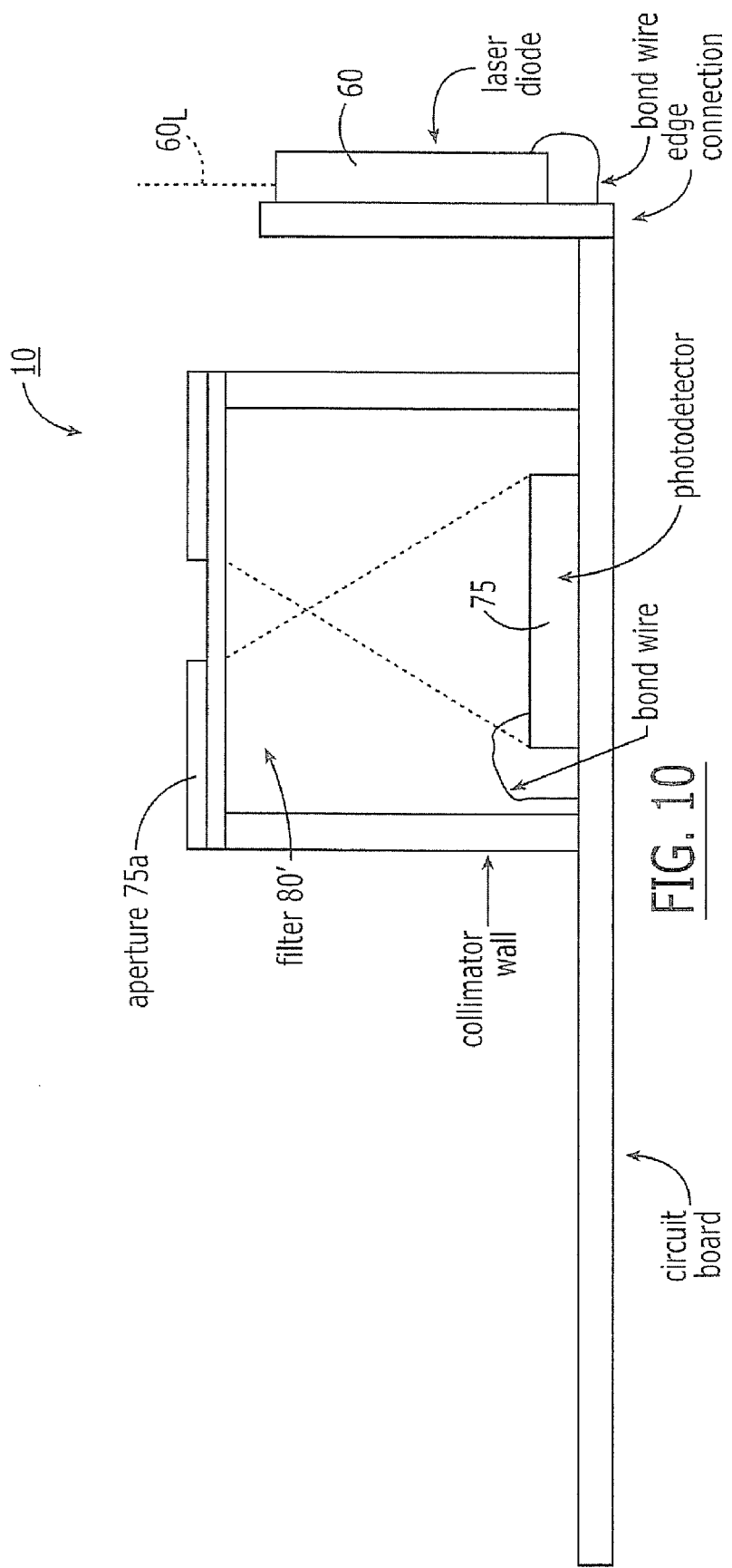
FIG. 10 is a schematic illustration of a sensor fluorescence excitation and detection configuration according to embodiments of the present invention.

FIG. 10 shows a second embodiment of an optical window 60w and filter 80' configuration. In this embodiment, a second filter is disposed above and spaced apart from the laser 60 and acts as a shifter 60s. The shifter 60s abuts the interface of the inner wall with the cylindrical filter 80c and directs the excitation light out of the sensor.

Alternatively, the laser light $60_L$ can be directed to hit the cylinder wall 10w at a steep angle (typically between about 75-105 degrees) to direct the excitation laser light to project right out of the sensor as shown in FIG. 11C. This configuration may be easier to implement than putting the shifter section up against the wall of the cylindrical filter 80c.

In some embodiments according to the present invention, Ab attachment at a tumor site or at a non-specific, non-tumor site can be monitored. Normal tissue can also be monitored to make sure it's not attacked. In some embodiments according to the present invention, the expression of protein resultant from a gene therapy modification can be monitored. In some embodiments according to the present invention, changes in cellular properties such as the onset of apoptosis or necrosis can be monitored using, for example, an exogenously introduced fluor or a matrix release method such as that discussed above. In some embodiments according to the present invention, the implantable device can be positioned over a wide range of depths inside a body.

The above will now be described with reference to the following non-limiting examples.

EXAMPLES

The fluorescence sensor systems described herein provide real-time, acute and/or chronic, measurement of fluorescently labeled analytes in vivo allowing pharmacokinetics and pharmacodynamics of antibody-based therapies to be assessed on an individualized basis. Initial experiments were successfully completed with a catheter-based version of the probe. The probe uses a laser diode illumination source and an optical multichannel analyzer. The laser diode (650 nm) source effectively penetrates several millimeters of tissue. The antibodies were labeled with Alexa 647 fluorophore (Molecular Probes, Eugene, Oreg.). In vitro tests confirmed this wavelength provides good light transmission through blood, tissue, and serum. Calibration studies with fluor in a colloidal gelatin mixture demonstrated sensitivity in the <10 ng/ml range.

Experiments were performed using two human cancer cell lines: Raji Burkitt's human lymphoma and BT474 human breast adenocarcinoma. The targeted antigens were, respectively, CD20 and HER2/neu (c-erbB2). HERCEPTIN (Genentech) and commercially available ANTI-CD20 (LabVision) were fluorescently tagged, applied to the appropriate cell line, and imaged under a confocal microscope at the appropriate wavelength. Both Raji and BT474 cells stained well, proving the labeling system was effective in reaching the target antigens. The fluorescent probe's molecular weight (under 800 Daltons) is small in comparison to antibodies and does not affect their binding capabilities.

In vivo experiments were undertaken to assess the probe's ability to monitor fluorescently conjugated antibodies and their uptake at the site of interest. The two tumor cell lines were ectopically implanted in nude mice (flank and scapular placements). In the BT474 model, a bolus of Alexa 647 labeled HERCEPTIN was injected into the tail vein at a dose of 3-5 mg/kg animal weight (clinical dose is ~4 mg/kg). The fiber probe, implanted at the site of the scapular tumor, showed moderate uptake of fluor in the tumor within several hours after injection (injection of Alexa 647 hydrazide alone showed peak uptake within minutes of injection). After 17 hours, external probing showed normal tissue measured slightly higher than baseline readings while both tumor sites were significantly higher, indicating that the tagged antibody had attached to the targeted antigen in the tumor tissue. Similar results were obtained with the CD20 system.

Other positive and negative controls were established to validate the results of the aforementioned experiments. Overall, the fluorescence probe shows strong potential for measuring antibody uptake in vivo at clinically relevant concentrations and assessing therapy effectiveness (i.e., uptake dynamics) and provides a platform for a wide range of research and diagnostic studies. It is contemplated that the device can be configured to allow placement substantially anywhere in the body so that assays of this sort will not be limited to surface probing.

In vitro tests were performed using two human cancer cell lines: Raji Burkitt's human lymphoma and BT474 human breast adenocarcinoma (both obtained from Wake Forest University). The targeted antigens for the experiments were CD20 for the Raji line and HER2/neu (c-erbB2) for the BT474 cells. Primary antibodies for HER2/neu included mouse monoclonal antibody anti-cerbB2 (LabVision, Inc.: Freemont, Calif.) and Genentech's (San Francisco, Calif.) commercially available drug for breast cancer, HERCEPTIN, for the BT474 cells. HERCEPTIN, along with RITUXAN (Genentech and IDEC, San Diego, Calif.) were the first two immunotherapy drugs approved by the FDA. HERCEPTIN targets breast cancer while RITUXAN targets CD20 positive, B-cell, non-Hodgkin's lymphomas. RITUXAN was not available for use at the time of these experiments so a commercially available mouse monoclonal antibody, ANTI-CD20 (LabVision, Inc.), was used with the Raji cells. In some cases the primary antibody was labeled with the fluorophore, but for the most part cellular microscopy utilizes a secondary labeled antibody to amplify the signal. The secondary antibody used was a goat anti-mouse IgG (H+L) from Molecular Probes (Eugene, Oreg.) labeled with an appropriate fluor of a different wavelength than the primary.

Figure 4:
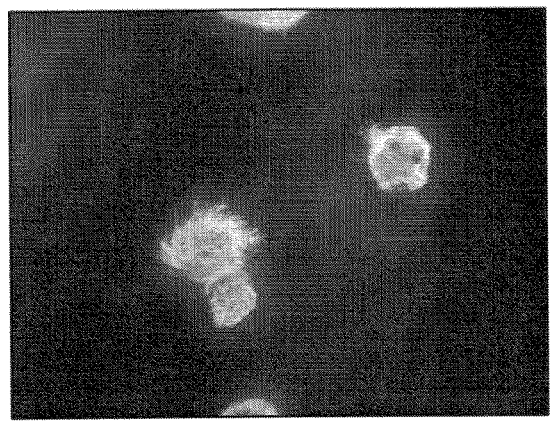
FIG. 4 is a digital image of a microscope view of Raji human lymphoma cells (in pellet form) labeled with ALEXA FLUOR 647 conjugated to ANTI-CD20.
Figure 5A:
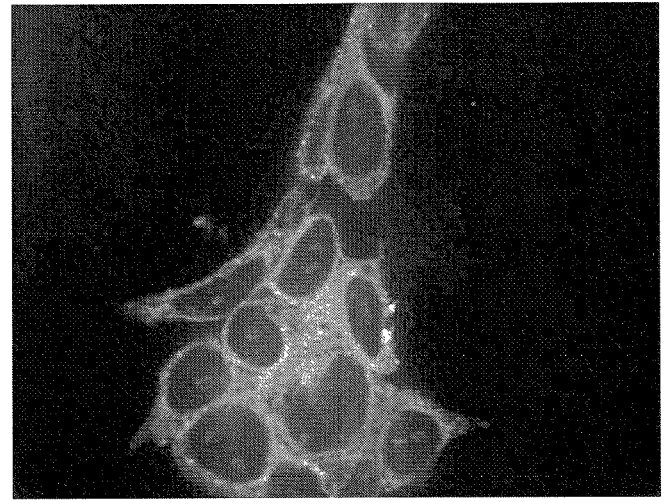
FIGS. 5A and 5B are confocal microscope images of BT474 cells fixed and labeled with ANTI-CERBB2 (LabVision, Inc.).
Figure 5B:
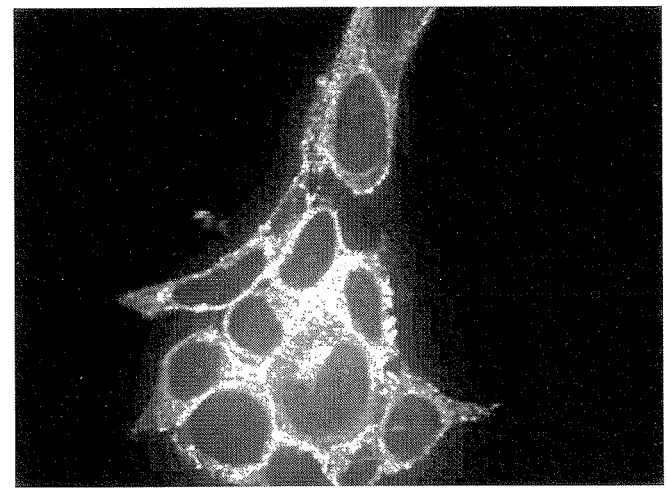

FIGS. 4, 5A & 5B show the type of images yielded by these analyses. These tests show that the labeling system can be effective in reaching the target. The in vivo fluorprobe may be sensitive to individual cells or, in other embodiments, sensitive to collections or clusters of cells in a discrete tumor. Regarding FIG. 5A/5B, the BT474 cells shown stain well in a cell surface, membrane localized pattern. This staining is present after two common methods of fixation, with a commercial mouse anti-cerbB2 antibody, but only when imaged via a species-specific secondary antibody that was itself independently labeled with a different color fluor. The fixed cells were labeled with ALEXA FLUOR 647 conjugated to anti-cerbB2 (primary) and ALEXA FLUOR 594 conjugated to goat anti-mouse IgG H+L (secondary antibody, Molecular Probes, Inc.). The images were made with a 568 nm or 647 nm line of a 100 mW Krypton/Argon laser and captured with a Hamamatsu Orca ER 12 bit camera through a Yokagawa brand spinning Nipkow disc.

The intensity of labeling can be a function of the concentration of primary antibody, since a tenfold increase in primary antibody concentration was visible by imaging the primary antibody's own fluorescent conjugate, as well as indirectly via the secondary antibody. In cell labeling experiments, this protocol of double labeling with a primary and secondary antibody is quite common as the secondary amplifies the signal given the present limited methods of detecting labeling. This labeling was deemed to be specific, since it was only weakly present in the presence of either the wrong primary antibody, or no primary antibody, and this weak staining did not show the strong "ring-like" localization to the plasma membrane as revealed by confocal microscopy. Some c-erbB2 antigen is present on all cells and over expressed on BT474 cells, so these results were expected.

To test the clearing of unbound fluors, a Fisher 344 rat was subcutaneously implanted with the catheter-based version of the fluorescence probe. The rat was injected via the tail vein at time 0 with 10 μg ALEXA FLUOR 594, and its uptake at the site of implantation was monitored for approximately 45 minutes (see FIG. 6). The fluor peaked approximately 30 seconds after injection and gradually decreased. A relatively high intensity was still detected at 45 minutes at the site of monoclonal antibody, ANTI-CD20 (LabVision, Inc.), was used with the Raji cells. There is a concentration of the cells around the membrane. The images were made with a 647 nm line of a 100 mW Krypton/Argon laser, using exciter filter 647/10 and emitter 700/75, and captured with a Hamamatsu Orca ER 12 bit camera through a Yokagawa brand spinning Nipkow disc. In some cases the primary antibody was labeled with the fluorophore, but for the most part cellular microscopy utilizes a secondary labeled antibody to amplify the signal. The secondary antibody used was a goat anti-mouse IgG (H+L) from Molecular Probes (Eugene, Oreg.) labeled with an appropriate fluor of a different wavelength than the primary.

Other in vivo experiments have also shown promising results for the fluorprobe's ability to track fluorescently conjugated antibodies and their uptake at the site of interest. Nude mice were implanted with human tumor xenografts of BT474 and Raji Burkitt's lymphoma cells. The tumors were allowed to grow until a palpable tumor was present. The mice were anesthetized with ketamine/xylazene and injected intravenously via the tail vein with either HERCEPTIN (one of the two FDA approved immunotherapy agents, Genentech Inc.) for the BT474 tumors or commercially available ANTI-CD20 (LabVision, Inc.) for the Raji humors. Positive and negative controls were also established. In vivo experiments are shown in Table 4.

TABLE 4

| Experiment | Results Summary |
| --- | --- |
| ALEXA FLUOR 594 HYDRAZIDE injected IV via tail vein of Fisher 344 rat. Probe placed subcutaneously in normal scapular tissue. | Fluor intensity signal peaked within 30 s and gradually decreased. Still relatively high at 45 min, when probe was removed. External probing in ear, tail vein, and excreted urine showed fluor was present. |
| ALEXA FLUOR 647 labeled HERCEPTIN injected IV via tail vein in nude mouse with scapular and flank BT474 tumors. Probe placed subcutaneously in scapular tumor. | Moderate uptake in tumor within several hours after injection. Slight increase in normal tissue relative to pre-injection readings. After 17 hours, normal tissue was slightly higher while both tumor |

TABLE 4-continued

| Experiment | Results Summary |
|---|---|
|  | tissues were significantly high, indicating that antibody had attached to tumor. Probe was used externally in the measurements made after 17 hours. |
| ALEXA FLUOR 647 labeled HERCEPTIN injected IV via tail vein in nude mouse with scapular and flank BT474 tumors. Probe placed subcutaneously in scapular tumor. | Same results as above with HERCEPTIN. |
| ALEXA 647 labeled HERCEPTIN injected IV via tail vein in nude mouse with no tumors. Probe placed subcutaneously in scapular tissue. | Peak uptake occurred within minutes. Signal intensity was equal to that previously seen in normal tissue of HERCEPTIN experiments. External probing showed it was fairly equally distributed throughout the body, and may have been slightly higher in mammary tissue. |
| ALEXA FLUOR 647 labeled ANTI-CD20 in Raji tumor on nude mouse. Probe placed subcutaneously in large tumor (~1000 mg). | Within a couple hours after injection, tumor signal continued to rise. After 17 hours, external probing showed that fluor uptake in tumor was significantly higher than in normal tissue. |
| ALEXA FLUOR 647 labeled ANTI-CD20 in BT474 tumor on nude mouse. Probe was placed subcutaneously in tumor. | Tumor had slightly preferential uptake over normal tissue, but not nearly as significant as with the HERCEPTIN experiments. Tumor may have some CD20 antigen present. Repeat experiment. |
| ALEXA FLUOR 647 HYDRAZIDE in normal tissue of nude mouse. Probe placed subcutaneously in normal tissue. | Fluor was observed within 10 min and peak intensity occurred within 30 min, much faster than with fluor conjugated to antibody. Probed scapula, flank, base of skull, kidney, and tail vein. All had approximately the same amount of signal intensity. |
| Naturally fluorescent BACPTDP (excites at 405 nm) injected into nude mouse implanted with human brain tumor cells on right flank. No visible or palpable signs of tumor. Signal was obtained from ex vivo placement of fiber probe. 500 nm emission filter used. | Signal was observed in tail vein immediately after injection and also in ear within first couple minutes after injection. No significant signal after the first couple minutes. Some signal fluctuation in ear, probably due to fiber positioning. Largest signal was found in right flank, where tumor cells were implanted. No sign of tumor growth, so need to repeat experiment to verify results. No significant signal anywhere else. The necropsy showed that almost all the fluor had accumulated in the gall bladder, consistent with the lack of signal elsewhere in the body and the fact that no sign of tumor was evident. |

FIGS. 7 & 8 show the uptake of labeled HERCEPTIN in BT474 tumors and ANTI-CD20 in Raji lymphoma tumors. It is noted that clinically appropriate dose levels of Ab were administered. The signal in tumor was significantly higher than in normal tissue, or than the baseline signal taken pre-injection in the tumor itself. The peak uptake was not reached until many hours after injection, confirming that antibody uptake can be slower than that of the fluor itself. Again, as seen in FIG. 6, fluor alone was tested and its peak intensity was reached in less than half an hour, indicating that for the experiments where tagged antibodies were used, the fluor did not significantly dissociate from the antibody. These experimental results indicate in vivo fluorescence probes of the present invention can provide clinically useful data.

It is anticipated that further evaluations can be carried out to determine tumor tissue pharmacokinetics (PK) of fluorescently labeled HERCEPTIN in 3 different mammary tumor lines that vary in levels of expression of Her2/neu. Human tumors could be implanted ectopically and orthotopically in the flank and scapular region of nude mice, as there are indications that the microenvironment and thus antibody behavior may differ between the two sites. Human tumor cell lines are available from several laboratories. MCF7 and BT474 human breast adenocarcinomas over express HER2/neu, or c-erbB2, to which the drug HERCEPTIN or any anti-HER2/neu (or anti-c-erbB2) antibody binds. The tumor lines used could be:

(1) BT474—Overexpresses supraclinical levels of HER2/neu.

(2) MCF7-Does not express HER2/neu.

(3) MCF7TamR—Developed at Duke by Drs. Dewhirst, Blackwell and McDonnell. It overexpresses HER2/neu at clinically relevant levels.

Female mice can be transplanted with the tumor cells in either the flank or the mammary fat pad and tumors allowed to grow to 8-9 mm in diameter. Animals transplanted with the MCF7 line will have estrogen (MCF7 and MCF7-Her2) and tamoxifen pellets (MCF7TamR only) implanted several days before tumor transplant. When the tumors have reached the analysis size, fluorescently labeled HERCEPTIN could be administered either as a bolus or infusion, IV, and fluorescence intensity measured non-invasively in the tumors every 1-2 hours for 48 hr, followed by measurements every 6-12 hours for six additional time points. At the end of the experiments, tumors can be removed and snap frozen for later sectioning and fluorescence intensity imaging. The kinetics of uptake and binding can be monitored until maximum binding (saturation) is achieved. The time points at which data is obtained or the longevity of the experiment may be adjusted according to the results of the first several experiments. Comparative spectral samples are taken non-invasively at the same time points in collateral normal tissue (e.g., muscle) and the tumor to muscle ratio is calculated. Sampling is performed frequently enough to obtain good estimates of the integrated amount (AUC) of antibody reaching the tumor. Each experiment may include four groups of five mice each—HERCEPTIN vs. non-specific control antibody and flank vs. orthotopic growth. Thus 20 mice can be used for each cell line, and this plan can be followed for 3 different cell lines (MCF7, BT474, MCF7TamR), yielding a total of 60 mice.

It is anticipated that: (a) the AUC for HERCEPTIN will be greater for the Her2 overexpressing lines than for the Her2 negative line; (b) the AUC for HERCEPTIN will be greater than the non-specific MOAb in Her2(+) lines, but will be equivalent to the non-specific MOAb in the MCF7 line; (c) within the Her2(+) lines, the AUC will be greatest for BT474, intermediate for MCF7Her2, and lowest for MCF7TamR; (d) HERCEPTIN uptake may be greater when the tumor is grown in the orthotopic site as compared to the ectopic site.

Kinetic analyses can be used to establish optimal sampling times to obtain plasma PK data.

Fluorescence intensity measurements made in the eye can be used as a surrogate for direct plasma measurements; and tumor tissue levels of antibody can be determined directly from frozen sections. One of the two Her2(+) lines can be used. Experiments can be conducted in one tumor site—most likely the orthotopic site. This experiment could require 5 animals per group×six (6) time points×one (1) tumor line× two (2) antibodies=60 mice. At the time points defined, animals with tumors that have received HERCEPTIN or control antibody can have measurements of fluorescence intensity made in the eye, fluorescence measurement of the tumor and a normal tissue site will be completed, and plasma will be obtained via retroorbital puncture for direct measurement of fluorescence intensity. The animals will then be analyzed for tumor tissue removal and snap freezing. The tumors can be cryosectioned and analyzed for fluorescence intensity. Plasma pharmacokinetics, relative fluorescence intensity in the eye as a function of time, and relative tissue concentration distribution of fluorescently labeled antibody can be established. It is anticipated that: (a) the pharmacokinetics of the measurements made in the eye and those of the direct plasma measurement will be similar, when normalized to peak values; (b) fluorescence intensity of frozen sections will be similar to those obtained with the fiber optic method, when normalized to peak values; (c) there will be less heterogeneity of antibody uptake with the specific antibody than the control antibody.

Figure 15:
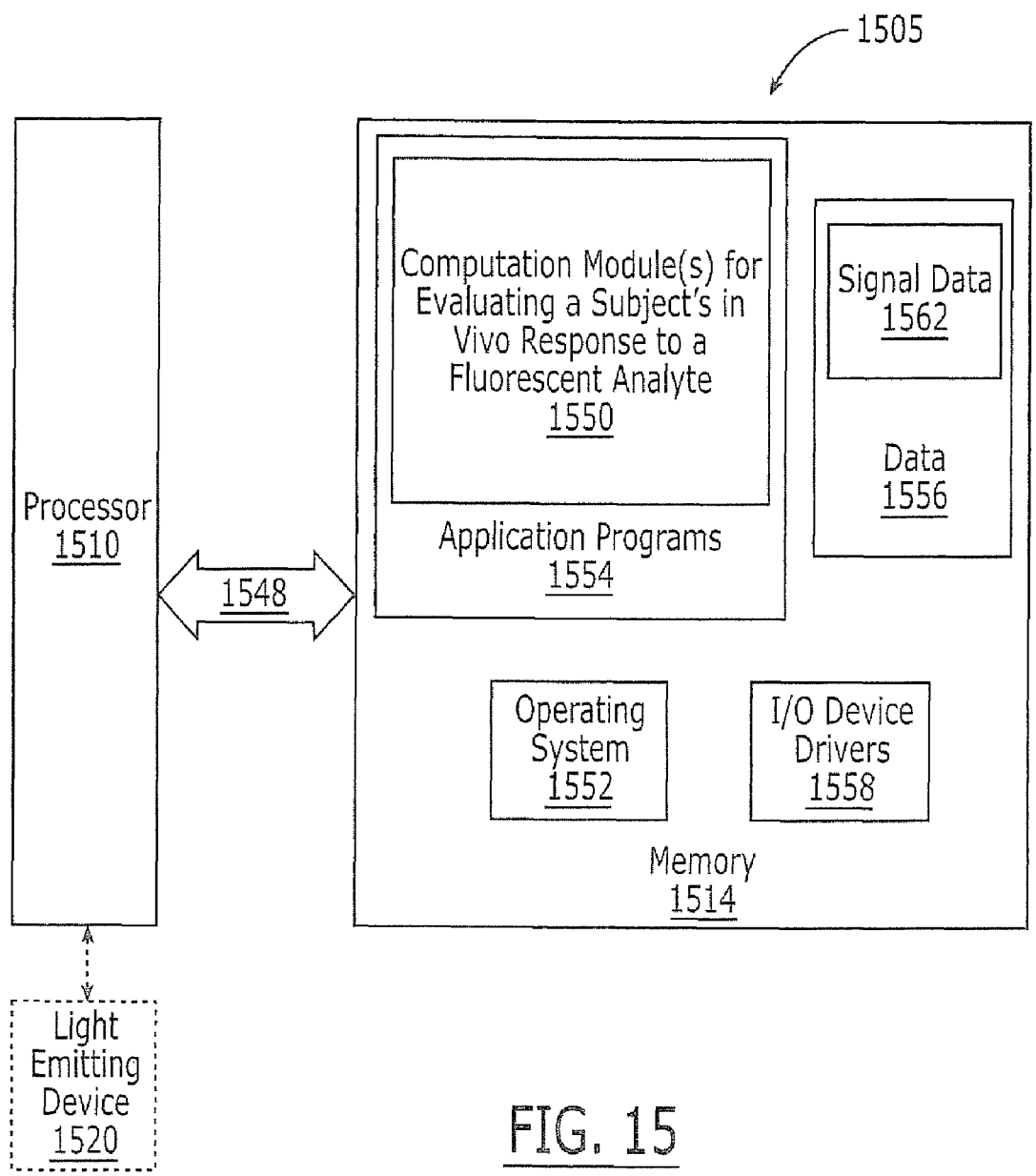
FIG. 15 is a block diagram of data processing systems and/or computer modules according to some embodiments of the present invention.

Referring now to FIG. 15, a block diagram of data processing systems 1505 according to embodiments of the present invention will be discussed. As illustrated in FIG. 15, the data processing system 1505 includes a computation module 1550 in accordance with embodiments of the present invention. The processor 1510 communicates with the memory 1514 via an address/data bus 1548. The processor 1510 can be any commercially available processor or may be a custom microprocessor. The memory 1514 is representative of the overall hierarchy of memory devices containing the software and data used to implement the functionality of the data processing system 1505. The memory 1514 can include, but is not limited to, the following types of devices: cache, ROM, PROM, EPROM, EEPROM, flash memory, SRAM, and DRAM.

As shown in FIG. 15, the memory 1514 may include several categories of software and data used in the data processing system 1505: the operating system 1552; the application programs 1554; the input/output (I/O) device drivers 1558; a computation module 1550; and the data 1556. The computation module 1550 includes computer program code that evaluates a subject's in vivo response to an administered fluorescent analyte. In certain embodiments, the fluorescent analyte includes a fluorescently pre-labeled analyte, a naturally fluorescent analyte and/or and analyte that exhibits fluorescence when internally administered to a subject.

The data 1556 may include fluorescence intensity signal data 1562 associated with detected fluorescence which may be obtained from one or more implanted sensors. The processor 1510 may communicate with one or more light emitting device 1520, for example, a fluorescence sensor configured for in vivo operation.

As will be appreciated by those of skill in the art, the operating system 1552 may be any operating system suitable for use with a data processing system, such as OS/2, AIX or OS/390 from International Business Machines Corporation, Armonk, N.Y., WindowsCE, WindowsNT, Windows95, Windows98, Windows2000, WindowsXP or Windows XT from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 1558 typically include software routines accessed through the operating system 1552 by the application programs 1554 to communicate with devices such as I/O data port(s), data storage 1556 and certain memory 1514 components and/or the light emitting device 1520. The application programs 1554 are illustrative of the programs that implement the various features of the data processing system 1505 and preferably include at least one application that supports operations according to embodiments of the present invention. Finally, the data 1556 represents the static and dynamic data used by the application programs 1554, the operating system 1552, the I/O device drivers 1558, and other software programs that may reside in the memory 1514.

While the present invention is illustrated, for example, with reference to the computation module 1550 being an application program in FIG. 15, as will be appreciated by those of skill in the art, other configurations may also be utilized while still benefiting from the teachings of the present invention. For example, the module 1550 may also be incorporated into the operating system 1552, the I/O device drivers 1558 or other such logical division of the data processing system 1505. Thus, the present invention should not be construed as limited to the configuration of FIG. 15, which is intended to encompass any configuration capable of carrying out the operations described herein.

The I/O data port can be used to transfer information between the data processing system 1505 and the system 1520 or another computer system or a network (e.g., the Internet) or to other devices controlled by the processor. These components may be conventional components such as those used in many conventional data processing systems, which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 15 but is intended to encompass any configuration capable of carrying out the operations described herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for determining in vivo fluorescent activity in a subject, comprising:
    positioning at least one sensor in tissue in a region of interest in the body;
    administering a fluorescent analyte to a subject, the fluorescent analyte including at least one of a fluorescently pre-labeled analyte, a naturally fluorescent analyte and an analyte that exhibits fluorescence when internally administered to the subject, wherein the fluorescent analyte is administered from a source other than the at least one sensor;
    emitting at least one excitation light signal from the at least one sensor to localized tissue proximate the at least one sensor, wherein the sensor projects the at least one excitation light signal outside the sensor at a distance sufficient to probe fluorescent activity at locations away from the sensor of several millimeters, wherein the excitation light signal has a wavelength that is between about 400 nm to about 900 nm;
    detecting in vivo from the at least one sensor a signal corresponding to fluorescence in the subject responsive to the administering and emitting steps;
    relaying the signal to a location external of the subject's body;
    electronically monitoring the relayed signal over time to electronically generate a time-dependent measurement profile of fluorescence in the localized tissue; and
    determining in vivo fluorescent activity of the subject based on the monitoring step.

2. A method according to claim 1, wherein the administrating step comprises administering the fluorescently pre-labeled analyte, wherein the excitation light is able to penetrate tissue that is up to about 20 mm away, and wherein the excitation light signal wavelength is between about 630 to about 660 nm and generates fluorescence response wavelengths of from about 665 to about 695 nm.

3. A method according to claim 1, wherein administering comprises administering the fluorescently pre-labeled analyte, wherein the excitation light is able to penetrate tissue that is up to about 20 mm away, and wherein the excitation light signal wavelength is between about 400 to about 660 nm and generates fluorescence response wavelengths of from about 400 to about 695 nm.

4. A method according to claim 1, wherein the at least one sensor is adapted to be implanted in the body at subsurface depths up to about 25 cm.

5. A method according to claim 1, wherein the excitation light signal is generated by a pulsed laser diode.

6. A method according to claim 5, wherein the pulsed laser diode is operated with a frequency that is between about 10 Hz to about 1 KHz and with a duty cycle of between about 1 to about 10 percent.

7. A method according to claim 6, wherein the excitation signal has an associated operating level of from about 1 to about 20 mW.

8. A method according to claim 1, wherein the at least one excitation signal comprises a plurality of signals having a predetermined variation in output intensity, and wherein the detecting and monitoring steps are carried out to generate optical profiling data.

9. A method according to claim 1, wherein the at least one sensor is configured as a cylindrical encapsulated body having a cylindrical optical filter that selectively allows light associated with the fluorescent wavelengths of interest to travel into the interior of the sensor body.

10. A method according to claim 1, wherein administering comprises administering the fluorescently pre-labeled analyte, wherein the analyte is a therapeutic pharmaceutical drug configured to treat a selected physiologic or biologic condition, impairment, or disease, and wherein the fluorescence label is substantially transparent to the physiologic or biologic reaction of the drug in the body, and wherein said monitoring and determining steps are carried out to predict and/or assess the in vivo clinical efficacy and/or localized dose of a selected treatment.

11. A method according to claim 1, wherein the administrating step comprises administering the fluorescently pre-labeled analyte, wherein the analyte comprises an antibody configured to treat a selected physiologic or biologic condition, impairment, or disease, and wherein the fluorescence label is substantially transparent to the physiologic or biologic reaction of the antibody in the body, and wherein said monitoring and determining steps are carried out to: (a) predict or assess the in vivo clinical efficacy of the antibody treatment; (b) measure a localized dose of the antibody; and/or (c) adjust a therapeutic dose amount administered to the subject.

12. A method according to claim 1, wherein the administrating step comprises administering the fluorescently pre-labeled analyte, wherein the pre-labeled analyte is a fluor-labeled pharmaceutical grade version of a gene therapy analyte configured for administration to a human subject, the labeled version of being substantially transparent to the in vivo behavior of the non-labeled version.

13. A method according to claim 12, wherein the determining step is carried out to determine the expression of a protein resulting from the administered gene therapy.

14. A method according to claim 1, wherein the determining step determines whether at least one of uptake and retention of the fluorescent analyte in the localized region is above a predetermined threshold level and/or a rate of the increase and decay in signal strength of the relayed signal over time.

15. A method according to claim 1, wherein the determining step comprises determining a phenotypic response to the fluorescent analyte.

16. A method according to claim 1, wherein said determining step determines an amount of time the detected relayed signal remains above a threshold level, a time the relayed signal takes to reach a peak level, a time the relayed signal takes to decay to below a threshold value, and a rate of decay of the relayed signal from a peak to a threshold value.

17. A method according to claim 1, wherein said monitoring step monitors, over a period of at least about 1 hour from a time said administering step is initiated, wherein the determining step comprises electronically generating a time-response profile with at least one predictor variable derived therefrom associated with uptake and/or retention of fluorescence in localized tissue, the predictor variable including at least one of:
   (a) a time at which the detected peak fluorescence count occurs;
   (b) a rate of increase of detected fluorescence;
   (d) a rate of decrease of detected fluorescence;
   (e) a time at which the detected fluorescence falls a predetermined amount below a threshold or the peak detected value;
   (f) a duration that the detected signal increases in strength; and
   (g) a time during the monitored period when the detected signal begins to decay.

18. A method according to claim 1, wherein the fluorescent analyte is administered to the subject as a first test dose amount, wherein the determining step predicts whether the response of the subject to the first dose indicates a the likelihood of a favorable response to a selected treatment, and wherein said method further comprises the step of administering a second therapeutic dose of the analyte to the subject if a favorable response is indicated, and wherein the second therapeutic dose amount is greater than the first test dose amount.

19. A method according to claim 1, wherein administering comprises administering the fluorescently pre-labeled analyte and wherein said determining step electronically assesses a behavior of the labeled analyte in vivo in the localized tissue and generates a predictive treatment outcome of a corresponding non-labeled analyte based on the behavior of the labeled analyte.

20. A method according to claim 1, wherein the sensor is disposed proximate or in a cancerous tumor, and wherein said determining step comprises determining cancer cell sensitivity or receptiveness to the fluorescent analyte.

21. A method according to claim 1, wherein at least one of the at least one sensors is positioned in the body so as to be proximate a tumor, and wherein said administering step is first carried out at a time which is proximate to a first planned therapeutic treatment, and wherein said determining step further comprises determining if the tumor is likely to be responsive to the planned treatment, said method further comprising the steps of:
   administering a therapeutic treatment to the subject after the fluorescent analyte administering step;
   repeating said step of administering the fluorescent analyte after said step of administering a therapeutic treatment wherein the determining step is carried out to monitor changes in cell kinetics following the therapeutic treatment.

22. A method according to claim 1, wherein the step of positioning is carried out so that the sensor is chronically implanted in the subject.

23. A method according to claim 1, wherein the at least one sensor is a plurality of sensors, each positioned in different locations in the body of the subject, and wherein each of the plurality of sensors can be serially polled.

24. A method according to claim 1, wherein the step of positioning is carried out so that at least one sensor is positioned proximate to cancerous tissue and another sensor is positioned proximate to normal tissue, and wherein said determining step evaluates biokinetics of both normal and cancerous tissue.

25. A method according to claim 1, wherein at least one of said sensors is implanted in localized tissue in the target region of interest and configured to operate wirelessly such that said relaying step is carried out telemetrically.

26. A method according to claim 1, wherein administering comprises administering the fluorescently pre-labeled analyte, wherein the labeled analyte is a labeled version of a pharmaceutical product undergoing clinical evaluation, and wherein the determining step comprises determining whether the pharmaceutical product reaches the region of interest and/or the pharmacodynamics and/or pharmacokinetics thereof.

27. A method according to claim 1, wherein said detecting step is at least periodically performed over a period of time extending for at least between about 24-48 hours.

28. A method according to claim 1, wherein said detecting step is at least periodically performed over a period of time extending from about several seconds to about several minutes.

29. A method according to claim 1, wherein said determining step serially determines fluorescent intensity of the fluorescent analyte in the localized tissue at a plurality of points in time and then determines at least one of the pharmacokinetic, the pharmacodynamic, the biokinetic response to the fluorescent analyte and/or the bioactivity in tissue in the region of interest.

* * * * *

UNITED STATES PATENT AND TRADEMARK OFFICE
CERTIFICATE OF CORRECTION

PATENT NO. : 7,778,695 B2  Page 1 of 1
APPLICATION NO. : 12/389012
DATED : August 17, 2010
INVENTOR(S) : Black et al.

It is certified that error appears in the above-identified patent and that said Letters Patent is hereby corrected as shown below:

In the Claims:

Column 40, Claim 12, Line 58: Please correct "labeled version of being" to read --labeled version being--.

Column 41, Claim 18, Line 32: Please correct "response of the subject to the first dose indicates a the" to read -- response of the subject to the first dose indicates a --.

Signed and Sealed this

Seventh Day of December, 2010

David J. Kappos
*Director of the United States Patent and Trademark Office*